US011400282B2

(12) United States Patent
Marshall et al.

(10) Patent No.: US 11,400,282 B2
(45) Date of Patent: Aug. 2, 2022

(54) LEADED ELECTRICAL STIMULATION SYSTEM

(71) Applicant: Medtronic, Inc., Minneapolis, MN (US)

(72) Inventors: Mark T. Marshall, Forest Lake, MN (US); Teresa A. Whitman, Dayton, MN (US); Carla Pfeiffer, Anoka, MN (US); Thomas A. Anderson, New Hope, MN (US); Jean Rutten, Gulpen (NL); Paul Adams, Munstergeleen (NL); Antoine Camps, Eys Wittem (NL); Richard Cornelussen, Maastricht (NL); Ralph Leinders, Gulpen (NL)

(73) Assignee: Medtronic, Inc., Minneapolis, MN (US)

( * ) Notice: Subject to any disclaimer, the term of this patent is extended or adjusted under 35 U.S.C. 154(b) by 269 days.

(21) Appl. No.: 16/681,279

(22) Filed: Nov. 12, 2019

(65) Prior Publication Data
US 2020/0147365 A1 May 14, 2020

Related U.S. Application Data

(60) Provisional application No. 62/767,085, filed on Nov. 14, 2018.

(51) Int. Cl.
 *A61N 1/36* (2006.01)
 *A61N 1/05* (2006.01)
 *A61N 1/362* (2006.01)

(52) U.S. Cl.
 CPC ............. *A61N 1/059* (2013.01); *A61N 1/362* (2013.01)

(58) Field of Classification Search
 CPC ........ A61N 1/059; A61N 1/362; A61N 1/365; A61N 1/37512; A61N 1/3752; A61N 1/3756

See application file for complete search history.

(56) References Cited

U.S. PATENT DOCUMENTS 5,076,285 A    12/1991   Hess et al.
5,906,634 A *   5/1999   Flynn .................. A61N 1/3752
                                                                        607/37

(Continued)

FOREIGN PATENT DOCUMENTS

WO   2015078971 A2   6/2015
WO   2016161189 A1   10/2016

OTHER PUBLICATIONS

Clark, MD, et al., "Minimally invasive percutaneous pericardial ICD placement in an infant piglet model: Head-to-head comparison with an open surgical thoracotomy approach," 2016 heart Rhythm Society, vol. 13, No. 5, May 2016, pp. 1096-1104.

(Continued)

*Primary Examiner* — Rex R Holmes
(74) *Attorney, Agent, or Firm* — Shumaker & Sieffert, P.A.

(57) ABSTRACT

In some examples, an implantable medical device (IMD) that includes a pulse generator comprising a housing, electrodes, and circuitry configured to deliver cardiac pacing via the electrodes. The IMD may further include a lead including at least one of the electrodes, an elongate body, a fixation helix, and a connector segment. A width of the helix transverse to a longitudinal axis of the lead is greatest at a distal end of the helix. A proximal end of the elongate body may be connected to a distal end of the pulse generator, and the helix may be attached to a distal end of the elongate body. The pulse generator may include a first connector tab. A distal end of the connector segment may be configured to receive the proximal end of the elongate body and a proximal end of the connector segment may include at least one second connector member configured to engage the first connector tab.

9 Claims, 12 Drawing Sheets

(56) References Cited

U.S. PATENT DOCUMENTS

| | | | |
|---|---|---|---|
| 2006/0136027 A1 | 6/2006 | Westlund et al. | |
| 2011/0112619 A1* | 5/2011 | Foster .................. | A61N 1/0575 607/127 |
| 2015/0351660 A1* | 12/2015 | An ......................... | G16H 40/67 600/484 |

OTHER PUBLICATIONS (PCT/US2019/061153) PCT Notification of Transmittal of the International Search Report and the Written Opinion of the International Searching Authority, dated May 7, 2020, 9 pages.

\* cited by examiner

LEADED ELECTRICAL STIMULATION SYSTEM

This application claims the benefit of U.S. Provisional Patent Application Ser. No. 62/767,085, filed Nov. 14, 2018, the entire contents of which are incorporated herein by reference.

TECHNICAL FIELD

The disclosure relates generally to medical device systems and, more particularly, medical devices configured for cardiac therapy delivery.

BACKGROUND

Some types of implantable medical devices (IMDs), such as cardiac pacemakers or implantable cardioverter defibrillators systems, may be used to provide cardiac sensing and therapy for a patient via one or more electrodes. Some IMDs include an implantable pulse generator that includes a housing that encloses electronic components, which may be configured to be implanted subcutaneously in the chest of the patient or within a chamber of a heart of the patient, as examples. Some IMDs having a pulse generator that is configured to be implanted outside of the heart and may be connected to one or more implantable medical electrical leads that include one or more electrodes. The leads may be configured such that the electrodes may, as examples, be implanted within the heart, e.g., transvenous leads, or outside of the heart and vasculature, e.g., extravascular leads. Extravascular leads of such IMDs may be implanted such that the lead is positioned near or in contact with an exterior of the heart, substernally, or in other extravascular locations.

SUMMARY

In general, this disclosure is directed to examples of IMDs for delivering cardiac therapy (e.g., cardiac pacing) and cardiac sensing, and to techniques for manufacturing such IMDs. Example IMDs may include a pulse generator, a plurality of electrodes, and a lead connected to the pulse generator. The techniques may include assembling the lead and attaching the lead to the pulse generator.

As an example, a lead of an IMD may include an elongate body and a fixation helix attached to a distal end of the elongate body. Such a fixation helix may be configured to engage patient tissue, such as cardiac tissue, to secure the lead to the tissue. A width of the fixation helix may be greatest at a distal end of the fixation helix and, in some examples, the fixation helix tapers in increasing width from a proximal end of the fixation helix to a distal end of the fixation helix. The width of the fixation helix being greatest at the distal end of the fixation helix may enable the fixation helix to engage the tissue in response to rotation of the lead about a longitudinal axis of the lead when the lead, e.g., of a distal end of the lead and/or a portion of the lead including the fixation helix, is positioned substantially parallel to the tissue.

A lead of an IMD may include a connector segment configured to attach the lead to a housing of the IMD. The connector segment and pulse generator each may include one or more connector tabs. The connector tabs of the connector segment may be configured to engage the connector tabs of the pulse generator, such as by rotation of the lead relative to the pulse generator. Although the components of the IMDs and techniques are described herein primarily in the context of an IMD configured for delivering cardiac pacing and cardiac sensing, such components and techniques are applicable to IMDs configured to deliver other types of cardiac therapy.

IMDs that include a pulse generator implantable within a chamber of the heart (e.g., a ventricle) or that utilize transvenous leads may not be preferred for all patients. For example, some patients may not be ideal candidates for placement of an IMD or transvenous lead within a chamber of the heart or the vasculature, such as patients with difficult vascular access, children, and other patients for whom such placement may necessitate open chest surgery. Moreover, IMD pulse generators implanted in a chamber of a heart and/or transvenous leads may become fibrosed in the heart over time, making lead revision and procedures involving extraction of IMD components from the heart challenging. IMDs that include a pulse generator configured to be implanted outside of the heart and one or more extravascular leads may eliminate the need to implant an IMD housing or transvenous leads within the heart. Thus, IMDs that include a pulse generator configured to be implanted outside of the heart and one or more extravascular leads may be preferred for some patients.

In some extravascular IMD systems, the lead(s) may be implanted subcutaneously, substernally, or in other extravascular locations. For example, an extravascular lead may be configured to be positioned between a parietal pericardium (referred to herein as a "pericardium") and a visceral pericardium (referred to herein as "epicardium") of a patient such that one or more electrodes of the lead are positioned in close electrical contact with the epicardium and myocardium. Such lead positioning may enable an IMD connected to the lead to sense cardiac electrical signals and deliver cardiac therapy, such as pacing pulses, to the patient's heart via electrodes on the lead. In some instances, close proximity of the electrodes of the lead to the heart advantageously may reduce power consumption by reducing a threshold magnitude (e.g., amplitude and/or width) of pacing pulses generated by the IMD needed to achieve pacing capture, relative to IMD systems in which electrodes of a lead are positioned further from the heart.

In some such example IMDs, the extravascular lead may include a fixation mechanism, such as a fixation helix, attached to an elongate body of the lead. For example, a fixation helix may be positioned at a distal end of the elongate body. The fixation helix may be configured to engage tissue of the epicardium and myocardium to anchor the lead to the heart when the lead is rotated about a longitudinal axis thereof. Such anchoring of the lead to the heart advantageously may help maintain the lead in a desired position relative to one or more portions of the heart, which enable consistent delivery of pacing pulses to desired portions of the heart.

However, fixation helices having certain configurations may cause undesirable deformation of the lead and/or patient tissue when such fixation helices are anchored to the epicardium and myocardium. For example, a distal end of a fixation helix having a constant width (e.g., diameter), or having a smaller width at a distal end than at a proximal end of the helix, may not be configured to pierce the epicardium unless the helix is positioned at an angle to the epicardium. Positioning the helix at an angle to the epicardium may require a portion of the lead to be bent away from the epicardium, which may cause a distal end of the lead to be forced into the epicardium, thereby causing an indentation or other deformation of the epicardium and myocardium. Continued deformation of such tissues may adversely affect tissue structure or function. In addition, bending a portion of the lead away from the epicardium increases the distance between the electrodes of the lead and the epicardium, which may increase an amount of energy required to be generated by the IMD to achieve pacing capture. IMDs including lead fixation structures according to this disclosure may reduce the likelihood of these issues.

In some such example IMDs, a proximal end of the extravascular lead may be physically and electrically connected to other components of the IMD. For example, a proximal end of a conductive cable of a lead may be connected (e.g., welded) to a conductive pin extending distally of a distal end of a housing of the pulse generator of the IMD that encloses circuitry configured to deliver cardiac pacing. However, a point of connection between such a lead and other components of the IMD may be subjected to mechanical strain caused by movement of the lead and/or pulse generator relative to one another, which may adversely affect the mechanical or electrical integrity of one or more components of the IMD and/or a connection point between the lead and the pulse generator of the IMB.

Thus, example IMDs described herein may include a fixation helix having configurations that may enable anchoring of the helix to an epicardium in a position substantially parallel to the epicardium. For example, lead fixation helices having a width that increases from a proximal end of the helix to a distal end of the helix (e.g., such that a width of the helix is greatest at the distal end), may help improve clinical outcomes for the patient and/or facilitate a lead implantation procedure. In some examples, leads of the IMDs described herein may include a connector segment positioned at a proximal end of the lead. Such a connector segment may be configured to securely connect the lead to a pulse generator of the IMB in a manner that reduces mechanical strain on the components of the IMB that may be caused by movement of the lead and/or the pulse generator relative to one another.

In one example, an implantable medical device comprises: a pulse generator defining a proximal end and a distal end and comprising a housing; a plurality of electrodes; circuitry within the housing, the circuitry configured to deliver cardiac pacing via the electrodes; and a lead defining a longitudinal axis, wherein the lead comprises at least one of the electrodes, the lead further comprising: an elongate body defining a proximal end and a distal end, wherein the proximal end of the elongate body is connected to the distal end of the housing; and a fixation helix attached to the distal end of the elongate body and defining a proximal end and a distal end, wherein a width of the fixation helix transverse to the longitudinal axis is greatest at the distal end of the fixation helix.

In another example, an implantable medical device comprises: a pulse generator defining a proximal end and a distal end and comprising a housing, the distal end of the pulse generator comprising at least one first connector tab; a plurality of electrodes; circuitry within the housing, the circuitry configured to deliver cardiac pacing to the patient via the plurality of electrodes; and a lead defining a longitudinal axis, wherein the lead comprises at least one of the plurality of electrodes, the lead further comprising: an elongate body defining a proximal end and a distal end; and a connector segment defining a proximal end and a distal end, wherein the distal end of the connector segment is configured to receive the proximal end of the elongate body and the proximal end of the connector segment comprises at least one second connector, and wherein the first and second connector tabs are configured to be engaged by rotation of the connector segment about the longitudinal axis of the lead relative to the housing to attach the connector segment to the pulse generator.

In another example, a method of manufacturing an implantable medical device, the method comprises: assembling a lead defining a longitudinal axis and comprising at least one electrode, wherein assembling the lead comprises: attaching an elongate body defining a proximal end and a distal end to a connector segment defining a proximal end and a distal end, wherein the distal end of the connector segment is configured to receive the proximal end of the elongate body and the proximal end of the connector segment comprises at least one first connector tab, and wherein attaching the elongate body to the connector segment comprises inserting the proximal end of the elongate body into the distal end of the connector segment; and, after attaching the elongate body to the connector segment, attaching the connector segment to a pulse generator of the implantable medical device defining a proximal end and a distal end and comprising a housing, wherein the distal end of the pulse generator comprises at least one second connector tab, and wherein attaching the proximal end of the elongate body to the pulse generator comprises: positioning the proximal end of the connector segment to engage the at least one first connector tab and the at least one second connector tab and rotating the connector segment about the longitudinal axis of the lead relative to the housing.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
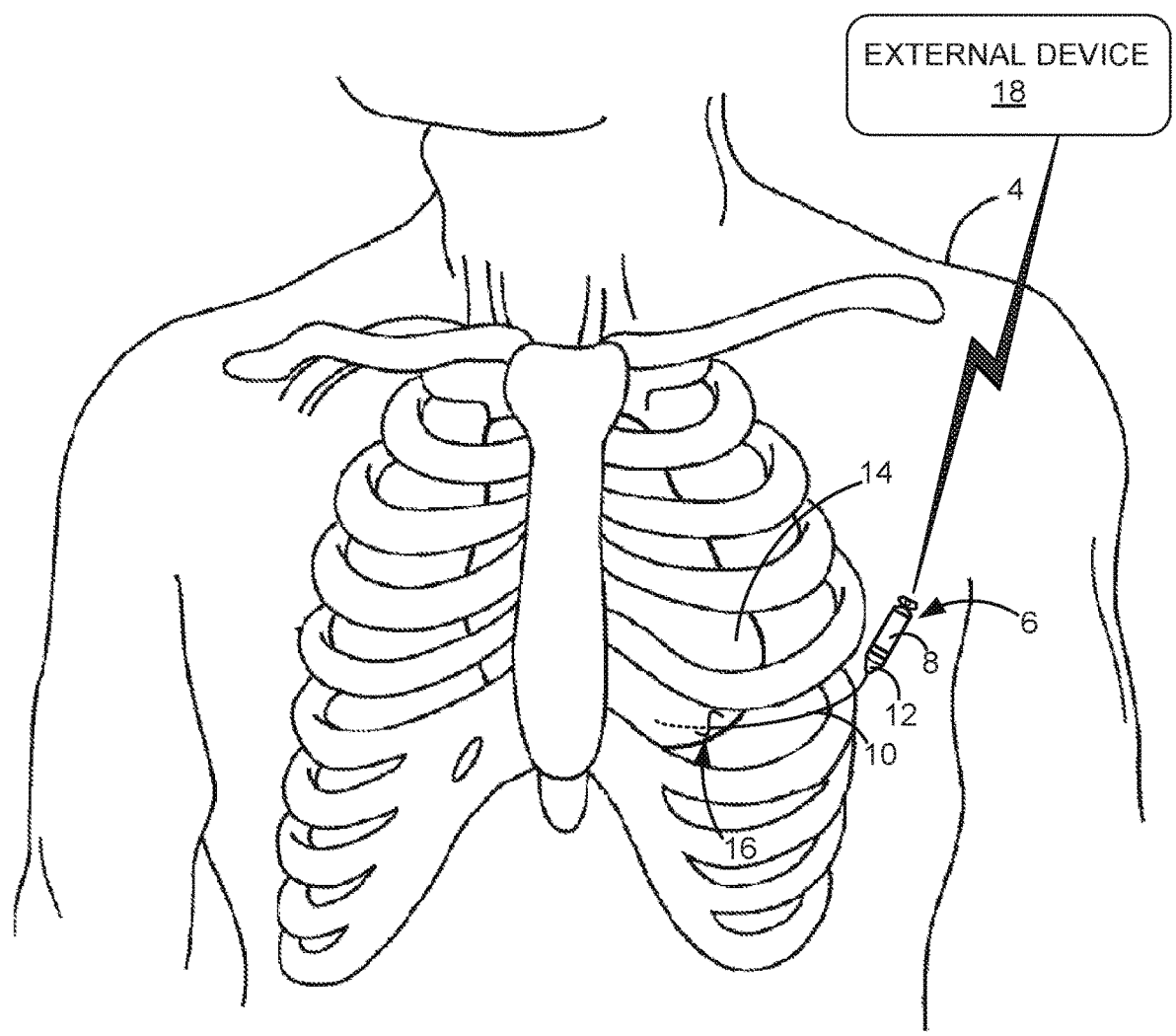
FIG. 1A is a conceptual drawing illustrating a front view of a patient with an example medical device system including an implantable medical device having a housing and a lead.

In general, this disclosure describes example IMDs. Such IMDs may include a pulse generator defining a proximal end and a distal end and a plurality of electrodes. The pulse generator may include a housing and circuitry within the housing configured to deliver cardiac pacing via the electrodes. Such IMDs also may include a lead. The lead may define a longitudinal axis and include at least one of the electrodes and an elongate body defining a proximal end and a distal end with the proximal end of the elongate body connected to the distal end of the pulse generator. In some examples, an IMD may include a fixation helix, which may be one of the plurality of electrodes, attached to the distal end of the elongate body and defining a proximal end and a distal end. A width of the fixation helix transverse to the longitudinal axis of the lead may be greatest at the distal end of the fixation helix (i.e., the width of the fixation helix at the distal end thereof is greater than widths of the fixation helix at longitudinal positions proximal of the distal end). The width of the fixation helix transverse to the longitudinal axis of the lead, at least at the distal end of the fixation helix, also is greater than a width (e.g., a circumference) of the elongate body of the lead. In some examples, the width of the fixation helix may increase from the proximal end to the distal end of the fixation helix such that the helix tapers in width from the proximal end to the distal end.

In some examples, the fixation helix may be configured to engage cardiac tissue (e.g., an epicardium) of a heart of the patient in response to rotation of the lead about the longitudinal axis of the lead while at least the portion of the lead including the fixation helix, e.g., including the distal end of the lead, is positioned substantially parallel to the epicardium. For example, the width of the fixation helix being greatest at the distal end of the fixation helix may enable the distal end of the fixation helix to engage the epicardium while at least the portion of the lead including the fixation helix and/or one or more other electrodes positioned on the lead is positioned substantially parallel to the epicardium. In some examples, the width of the distal end of the fixation helix being greater than a width of the elongate body of the lead also may help enable the distal end of the fixation helix to engage the epicardium in such a manner. For example, the difference between the width of the distal end of the fixation helix and the width of the elongate body may reduce a possibility of the elongate body mechanically interfering with the distal tip of the fixation helix during engagement of the distal tip of the fixation helix with the epicardium, such as by reducing a possibility of contact of the elongate body with the epicardium pushing the distal tip of the fixation helix away from the epicardium.

In some examples, the pulse generator may define a distal end that includes at least one first connector tab and the lead may include a connector segment defining a proximal end and a distal end. The distal end of the connector segment may be configured to receive the proximal end of the elongate body and the proximal end of the connector segment may include at least one second connector tab. The first and second connector tabs may be configured to be engaged by rotation of the connector segment about the longitudinal axis of the lead, relative to the pulse generator, to attach the connector segment to the pulse generator.

In some such examples, the IMD may include a conductive pin positioned to extend from within the pulse generator through the distal end of the pulse generator, and distally of the distal end of the pulse generator. The connector segment may further include a connector segment housing that defines a connector segment lumen extending from the proximal end of the connector segment to the distal end of the connector segment, and an adaptor received in the connector segment lumen and defining an adaptor proximal end, an adaptor distal end, and an adaptor lumen. At the proximal end of the adaptor, the adaptor lumen may be configured to receive the conductive pin. The adaptor may be conductive.

In some examples, the lead may include a first electrode of the plurality of electrodes and a second electrode of the plurality of electrodes. In such examples, the elongate body may include a first conductor and a second conductor. The first electrode may be coupled to the conductive pin via the first conductor, and the second electrode may be coupled to a portion of the pulse generator around the conductive pin via the second conductor and the adaptor. The IMD may further include a crimp core received within the adaptor lumen and configured to receive the proximal end of the elongate body, and the second conductor may be coiled around the crimp core and held in electrical contact with the adaptor by the crimp core.

In some examples in which the IMD includes the conductive pin, an elongate body of the lead may include a conductive cable defining a proximal end and a distal end and an insulative layer positioned around an outer surface of the conductive cable. Some examples further include an insulative coating between the outer surface of the conductive cable and the insulative layer. A proximal segment of the conductive cable that includes the proximal end of the conductive cable may extend into the connector segment lumen. In some examples, at least a portion of the proximal segment of the conductive cable may extend proximally of the insulative layer, i.e., the insulative layer may not extend to the proximal end of the conductive cable in such examples. Furthermore, a portion of the proximal segment of the conductive cable that is proximal to both the insulative layer and the inner insulative coating, e.g., the proximal end of the conductive cable, is welded or otherwise connected to the conductive pin.

The proximal segment of the conductive cable also may include an excess length of the conductive cable that may facilitate connection of the conductive cable to the conductive pin during manufacturing of the IMD, but which desirably may be re-positioned into a compact configuration following attachment of the conductive cable to the conductive pin. In such examples, the connector segment housing and the adaptor may define a channel extending from an outer surface of the connector segment housing radially inward to the connector segment lumen and further radially inward to the adaptor lumen. A portion of the proximal segment of the conductive cable, e.g., the portion that is proximal to the insulative layer and distal to the proximal end of the conductive cable, but which still may include the inner insulative coating, extends through the channel and exterior to the outer surface of the connector segment when the proximal end of the conductive cable is received within the connector segment lumen and the adaptor lumen and connected to the conductive pin. In some examples, the portion of the proximal segment that extends through the channel and exterior to the outer surface includes the insulative coating, but does not include insulative layer, e.g., to increase the flexibility of this portion.

The connector segment may be configured to draw the proximal segment of the conductive cable into the connector segment when the connector segment is rotated about the longitudinal axis of the lead such that the proximal segment of the conductive cable wraps around the adaptor. In such examples, rotation of the connector segment about the longitudinal axis of the lead, after the proximal end of the conductive cable has been connected to the conductive pin, may cause the proximal segment of the conductive cable extending through the channel to be drawn radially inward through the channel and wrapped about the adaptor such that a portion of the proximal segment of the conductive cable is positioned entirely within the connector segment and wrapped around the adaptor in a relatively more compact configuration. In some examples, the portion of the proximal segment of the conductive cable that is wrapped around the adaptor may function as a strain relief segment of the conductive cable. Such a strain relief segment of the conductive cable may reduce a transfer of motion from a distal portion of the conductive cable and/or the elongate body of the lead to the conductive cable and/or the connection between the conductive cable and the conductive pin.

In some examples, the connector segment may define an adhesive fill port that extends from the outer surface of the connector segment radially inward to the connector segment lumen. In some such examples, an adhesive material may be introduced into the adhesive fill port during manufacturing of the IMD, such as following connection of the lead to the pulse generator and rotation of the connector segment to draw the excess length of the conductive cable into the connector segment. The adhesive fill port may transmit an adhesive material introduced into the adhesive fill port to the connector segment lumen, thereby filling open spaces in the connector segment lumen with adhesive, which may help secure a connection between the elongate body and adaptor within the connector segment and/or help secure the connector segment to the pulse generator. In such a manner, the configuration and positioning of the connector segment may help securely connect the lead to the pulse generator and reduce mechanical strain on the components of the IMD (e.g., on the elongate body, conductive cable, or other components) that may be caused by movement of the lead and/or the pulse generator relative to one another.

Figure 1B:
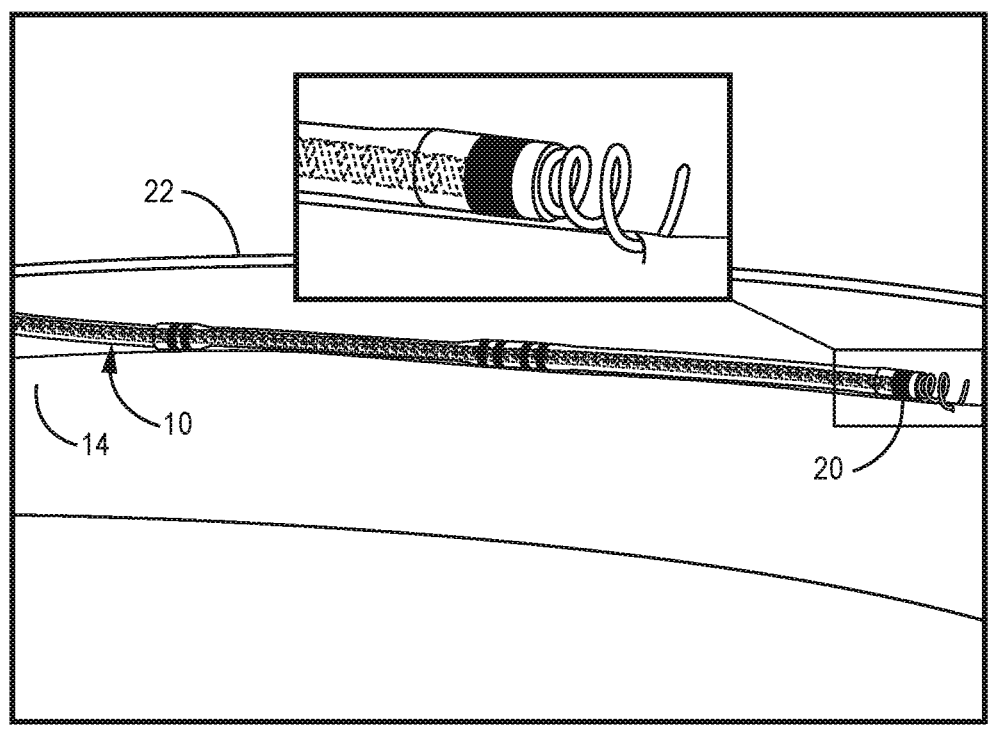
FIG. 1B is a conceptual drawing illustrating a side view of a lead of the example implantable medical device of FIG. 1A attached to an epicardium of the patient.

FIGS. 1A and 1B are conceptual diagrams of an extravascular IMD system 2 implanted within a patient 4. FIG. 1A is a front view of IMD system 2, which includes an IMD 6 that includes a pulse generator 8 and a lead 10, implanted within patient 4. FIG. 1B is a side view of lead 10 attached to an epicardium 14 of patient 4.

In the example illustrated in FIG. 1A, system 2 is an IMD system that provides pacing therapy. However, some of the components of the IMDs described herein, such as components configured to attach the lead to tissue or attach the lead to a housing of an IMD may be utilized with other types of IMDs, such as other IMDs configured to deliver cardiac electrical therapy. Although system 2 is described herein in the context of cardiac electrical therapy, one or more aspects of system 2 (e.g., a configuration of lead 10 and its connection to pulse generator 8) may be adapted to IMDs configured to deliver other types of electrical therapy to a patient.

In addition, it should be noted that system 2 may not be limited to treatment of a human patient. In alternative examples, IMD system 2 may be implemented in non-human patients, e.g., primates, canines, equines, pigs, ovines, bovines, and felines. These other animals may undergo clinical or research therapies that may benefit from the subject matter of this disclosure.

Pulse generator 8 of IMD 6 may include a hermetic seal that protects components of IMD 6. Pulse generator 8 may be formed of a conductive material, such as titanium, or of a combination of conductive and non-conductive materials. The conductive material of pulse generator 8 may function as a housing electrode. Lead 10 may include a connector segment 12 configured to connect an elongate body of lead 10 to pulse generator 8. The portion of pulse generator 8 adjacent connector segment 12 may include electrical feedthroughs (e.g., a conductive pin, as described below) through which electrical connections are made between lead 10 and electronic components included within pulse generator 8. In some examples, pulse generator 8 may house one or more of processing circuitry, memories, transmitters, receivers, sensors, sensing circuitry, therapy circuitry, power sources, or other suitable components.

IMD 6 is configured to be implanted in a patient, such as patient 4. In some examples, pulse generator 8 of IMD 6 may be implanted subcutaneously above a ribcage on the left side of patient 4. Pulse generator 8 may, in some examples, be implanted between the left posterior axillary line and the left anterior axillary line of patient 4. In other examples, pulse generator 8 may be implanted at other subcutaneous locations in patient 4, such as at a pectoral location, an abdominal location, or a subxiphoid location. In some examples, pulse generator 8 may be placed intrathoracically. In some such examples, pulse generator 8 may implanted under the xiphoid process or sternum, and lead 10 may extend through the diaphragmatic attachments under the sternum and into the pericardial space. As shown in FIG. 1A, lead 10 may extend from pulse generator 8 subcutaneously above a ribcage of patient 4, such as subcutaneously above an intercostal space of the left side of the ribcage (e.g., the fifth intercostal space) to a location near the center of the torso and substantially over heart 14. At the location near the center of the torso, lead 10 bends or turns toward an epicardium of heart 14. A distal end of lead 10 may be inserted into the epicardium at entry point 16 in the epicardium and tunneled between the epicardium and a pericardium of patient 4. However, in other examples, pulse generator 8 and/or lead 10 may be implanted in different locations within patient 4. For example, lead 10 may be positioned subcutaneously. In other examples, pulse generator 8 may be positioned externally of patient 4, such as in examples in which IMD 6 is configured to deliver temporary or "trial" electrical stimulation to patient 4. In some examples, one or more features of IMD 6 (e.g., a configuration of pulse generator 8) may be adapted to such different implantation locations. Thus, the example implantation locations of IMD 6 and types of electrical therapy that may be delivered by IMD 6 described herein are exemplary in nature and should not be considered limiting of the embodiments described herein.

In some examples, system 2 may include external device 18, as shown in FIG. 1A. External device 18 may be a computing device that is configured for use in a home, ambulatory, clinic, or hospital setting to communicate with IMD 6 via wireless telemetry. Examples of communication techniques used by IMD 6 and external device 18 include radiofrequency (RF) telemetry, which may include an RF link established via Bluetooth, wireless local networks, or medical implant communication service (MICS). The communication may include one-way communication in which one device is configured to transmit communication messages and the other device is configured to receive those messages. Alternatively, or additionally, the communication may include two-way communication in which each device is configured to transmit and receive communication messages.

External device 18 may include communication circuitry configured to communicate with one or more devices of system 2 (e.g., IMD 6) in accordance with the techniques described above. For example, external device 18 may be used to program commands or operating parameters of IMD 6 for controlling functioning of IMD 6 when external device 18 is configured as a programmer for IMD 6. External device 18 may be used to communicate with IMD 6 to retrieve data such as operational data, physiological data accumulated in IMD memory, or the like. As such, external device 18 may function as a programmer for IMD 6, an external monitor for IMD 6, or a consumer device such as a smartphone.

External device 18 may be coupled to a remote patient monitoring system, such as CARELINK®, available from Medtronic plc, of Dublin, Ireland. In other examples, a clinician may use external device 18 to program or update therapy parameters that define cardiac therapy, and/or program or update modifications to the cardiac therapy parameters, sensing parameters, and/or electrode vectors, or perform other activities with respect to IMD 6. The clinicians may be a physician, technician, surgeon, electrophysiologist, or other healthcare professional. In some examples, the user may be patient 4.

The distal portion of lead 10 includes a fixation helix 20 that is configured to engage cardiac tissue of heart 14 of patient 4, as shown in FIG. 1B. For the sake of clarity, the cardiac tissue engaged by fixation helix 20 may be referred to herein as being an epicardium of heart 14, though fixation helix 20 additionally may engage a myocardium and/or other tissue of heart 14. Fixation helix 20 may be configured to engage the epicardium of heart 14 in response to rotation of lead 10 about a longitudinal axis thereof, while lead 10 is positioned between the epicardium of heart 14 and a pericardium 22 of patient 4 such that at least a portion of lead 10 that includes fixation helix 20 and/or one or more other components of lead 10 (e.g., the distal portion of lead 10) is substantially parallel to the epicardium of heart 14 and to pericardium 22. For example, a width of fixation helix 20 may be greatest at a distal end of fixation helix 20. In some examples, the greatest width of fixation helix 20 may be greater than a width of a body of lead 10 proximal to fixation helix 20. As described in further detail with respect to FIG. 2, such a configuration of fixation helix 20 may help enable lead 10 to be attached to the epicardium of heart 14 such that at least the portion of lead 10 including fixation helix 20 and/or one or more other components of lead 10 is substantially parallel to the epicardium of heart 14 and to pericardium 22. In some examples, attaching lead 10 to the epicardium of heart 14 in such a manner may reduce a possibility of deformation of the epicardium of heart 14 and/or of pericardium 22.

With lead 10 attached to heart 14 such that at least the portion of lead 10 including fixation helix 20 and/or one or more other components of lead 10 is substantially parallel to the epicardium of heart 14 and to pericardium 22, one or more electrodes positioned on lead 10, which may include fixation helix 20, may be positioned to sense cardiac electrical signals and/or deliver electrical stimulation (e.g., cardiac pacing) to heart 14. Such positioning of lead 10 relative to heart 14 may place the one or more electrodes in contact with, or in close proximity to, the epicardium of heart 14. In some examples, positioning the one or more electrodes in contact with, or in close proximity to, the epicardium of heart 14 may reduce a threshold magnitude of pacing pulses needed to achieve pacing capture of heart 14, relative to electrode positions further from the heart 14. Thus, in some examples, attachment of lead 10 to the epicardium of heart 14 via fixation helix 20 advantageously may reduce power consumption of IMD 6, which may increase a longevity of a power source of IMD 6.

Figure 2:
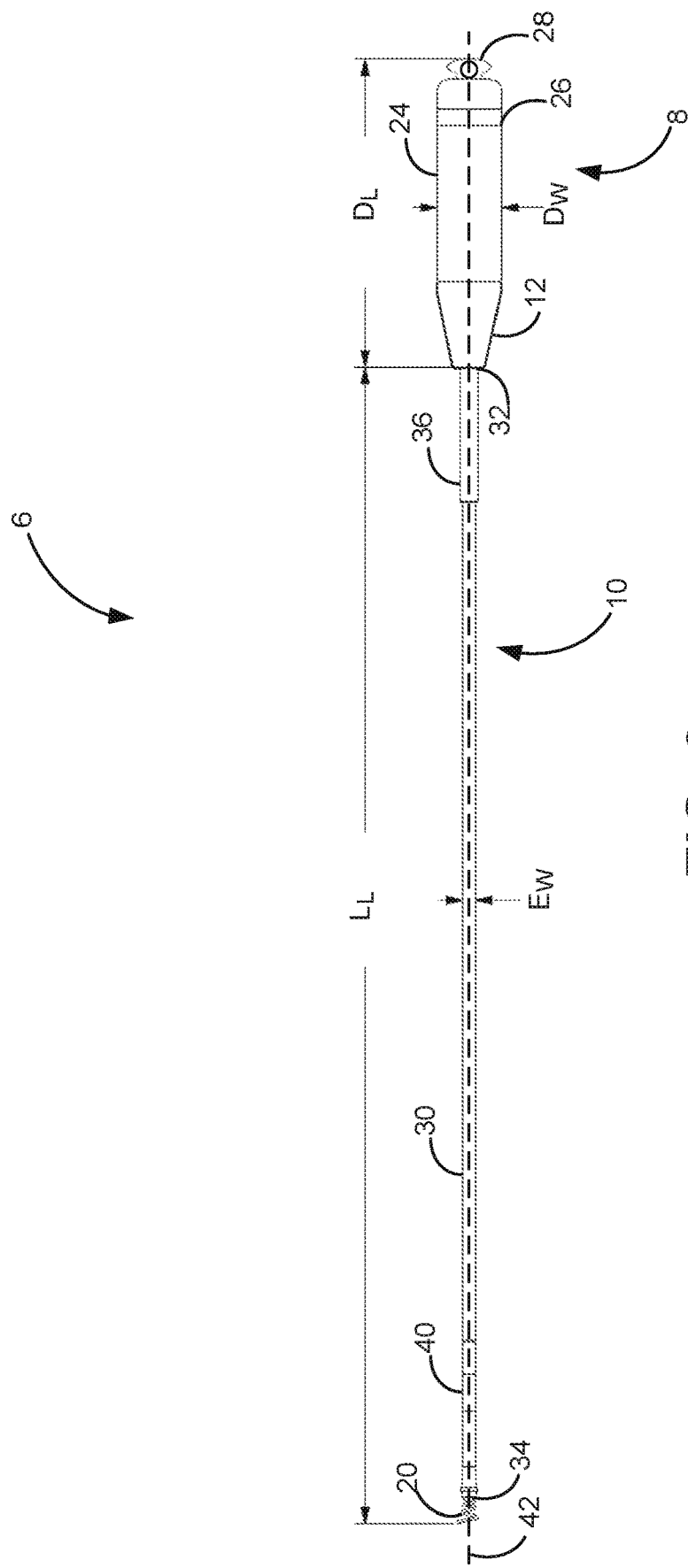
FIG. 2 is a side view of the implantable medical device of FIG. 1A.

FIGS. 2-7 illustrate components of IMD 6 in further detail. FIG. 2 is side view of IMD 6, including pulse generator 8, lead 10, and connector segment 12. In the example of FIG. 2, pulse generator 8 has a length $D_L$, which may be from about 1.2 centimeters (cm) to about 5.0 cm, and a width $D_W$, which may be from about 0.5 cm to about 0.8 cm. In some other examples, pulse generator 8 may have length $D_L$ of about 0.7 cm, and may have a width $D_W$ of about 0.4 cm. Pulse generator 8 includes a housing 24, which may be hermetically sealed to enclose and protect electrical components (e.g., processing circuitry, sensing circuitry, therapy delivery circuitry, or other components) within pulse generator 8. In some examples, housing 24 may enclose some or all of the electrical components of pulse generator 8, and a feedthrough may seal a distal end of housing 24 and create the hermetically sealed pulse generator 8. Both housing 24 and connector 12 may be electrically insulating.

In some examples, IMD 6 may include one or more electrodes in addition to fixation helix 20. In some such examples, generator 8 may include one or more electrodes 26, which may be configured to deliver an electrical signal (e.g., therapy such as cardiac pacing) and/or configured to provide at least one sensing vector. Electrode 26 may be a ring or cylindrical electrode carried on housing 24 of pulse generator 8. In this manner, electrode 26 may be considered a leadless electrode. In the example of FIG. 2, electrode 26 is disposed on an exterior surface of housing 24 and may be positioned to contact cardiac tissue upon implantation. In some examples, electrode 26 comprises more than one electrode 26. In such examples, one electrode 26 may be used as a cathode and another electrode may be used as an anode for delivering cardiac pacing, such as bradycardia pacing, CRT, ATP, or post-shock pacing. In addition, one or more electrodes 26 may be used to detect intrinsic electrical signals from heart 14, such as an electrocardiogram signal that processing circuitry enclosed within pulse generator 8 may receive via sensing circuitry enclosed within pulse generator 8.

Pulse generator 8 also may include a manipulator attachment feature 28, which may be positioned at a proximal end of pulse generator 8. In some examples, manipulator attachment feature 28 may be integral with housing 24. In other examples, manipulator attachment feature 28 may be a separate component of IMD 6 that is attached to housing 24. In any such examples, manipulator attachment feature 28 may have a configuration that defines an opening, a hook shape, or any other suitable configuration that may enable tethering or extraction of pulse generator 8 to or from patient tissue. For example, manipulator attachment feature 28 may be configured to receive or otherwise attach to a manipulator tool configured to enable a clinician to manipulate IMD 6, such as during a procedure to implant or explant IMD 6. In some examples, manipulator attachment feature may be configured to attach IMD 6 to patient tissue. For example, a suture or other device may be inserted around and/or through manipulator attachment feature 28 and attached to tissue. In this manner, manipulator attachment feature 28 may provide an attachment structure to tether or retain pulse generator 8 within patient tissue at an implant site of pulse generator 8. Manipulator attachment feature 28 also may be used to extract pulse generator 8 if IMD 6 is to be explanted (i.e., removed) from patient 4 if such action is deemed desirable.

In the example of FIG. 2, lead 10 has a length LL, which may be from about 5 cm to about 25 cm. Lead 10 includes connector segment 12, which is configured to connect lead 10 to the distal end of pulse generator 8, as further described below with respect to FIGS. 3 and 7. Lead 10 includes elongate body 30, which defines a proximal end 32 and a distal end 34. Elongate body 30 may have a generally uniform shape along the length of the lead body. In one example, elongate body 30 may have a generally tubular or cylindrical shape along the length from proximal end 32 to distal end 34, although other lead body designs may be used without departing from the scope of this disclosure. In some examples, elongate body 30 may have a substantially straight shape along a length thereof. In other examples, elongate body 30 may have a different shape along a length thereof, such as an undulate or otherwise curved shape. In any such examples, elongate body 30 may have a width $E_W$ (elongate body width), which may be from about 0.06 cm (about 2 French (Fr)) to about 0.19 (cm) (about 6 French). Elongate body 30 may be formed from a non-conductive material, including silicone, polyurethane, fluoropolymers, mixtures thereof, and other appropriate materials, and shaped to form one or more lumens within which one or more conductors (described below with respect to FIG. 3) extend. In some examples, lead 10 may include a strain relief 36 positioned around a proximal portion of elongate body 30. Strain relief 36 also may be formed from a non-conductive material, such as silicone tubing. In some examples, strain relief 36 may help relieve mechanical stress that may exerted on one or more conductors positioned within the proximal portion of elongate body 30 when pulse generator 8 and lead 10 are moved relative to one another, which may help improve a durability of the connections between elongate body 30 and connector segment 12.

Fixation helix 20 is positioned at distal end 34 of elongate body 30. In some examples, fixation helix 20 may be electrically connected to pulse generator 8 such that fixation helix 20 functions as an electrode (e.g., fixation helix 20 may be configured to sense electrical signals from heart 14 and/or deliver cardiac therapy to heart 14). As illustrated in FIG. 2, a width of fixation helix 20 may be greatest at a distal end of fixation helix 20, such that fixation helix 20 tapers in increasing width from a proximal end of fixation helix 20 to a distal end of fixation helix 20. In some examples, the width of the distal end of fixation helix 20 also may be greater than a width (e.g., a circumference) of elongate body 30.

The width of fixation helix 20 being greatest at its distal end, and/or the width of the distal end of fixation helix 20 being greater than a width of elongate body 30 at the distal end of fixation helix 20, may enable fixation helix 20 to engage tissue of heart 14 in response to rotation of lead 10 about a longitudinal axis 42 of IMD 6 (which may also be a longitudinal axis of lead 10) when at least the portion of lead 10 including fixation helix 20 and/or electrode 40 is positioned substantially parallel to the epicardium of heart 14. In such a manner, fixation helix 20 and/or at least a portion of elongate body 30 (e.g., at least a portion including electrode 40) are substantially parallel to the epicardium of heart 14 during and after implantation of lead 10. In some examples, the width of the distal end of fixation helix 20 being greater than a width of elongate body 30 may help enable the distal end of fixation helix 20 to engage the epicardium of heart 14 in such a manner. In some examples, the difference between the width of the distal end of fixation helix 20 and a width of elongate body 30 may reduce a possibility of elongate body 30 mechanically interfering with the distal tip of fixation helix 20 during engagement of the distal tip of fixation helix 20 with the epicardium, such as by reducing a possibility of contact of elongate body 30 with the epicardium pushing the distal tip of fixation helix 20 away from the epicardium.

Attaching lead 10 to the epicardium of heart 14 with fixation helix 20 and/or at least a portion of elongate body 30 positioned substantially parallel to the epicardium of heart 14 and pericardium 22 may reduce or substantially eliminate linear force exerted upon the outer surface of the epicardium of heart 14 by distal end 34 of elongate body 30, which may reduce deformation (e.g., indentation) of the epicardium of heart 14. Additionally, or alternatively, the configuration of fixation helix 20 that enables lead 10 to be attached to the epicardium of heart 14 with fixation helix 20 and/or at least a portion of elongate body 30 being positioned substantially parallel to the epicardium of heart 14 and pericardium 22 may help maintain elongate body 30 in contact with or in close proximity to the epicardium of heart 14 when lead 10 is attached to the epicardium of heart 14. Maintaining elongate body 30 in contact with or in close proximity to the epicardium of heart 14 may reduce a possibility of pericardium 22 being deformed by lead 10, and/or may help maintain one or more electrodes of lead 10, such as electrode 40, in contact with or in close proximity to the epicardium of heart 14, which may enable pacing pulses having a relatively low magnitude (e.g., relative to electrodes positioned further from heart 14) to achieve pacing capture of heart 14.

Figure 3:
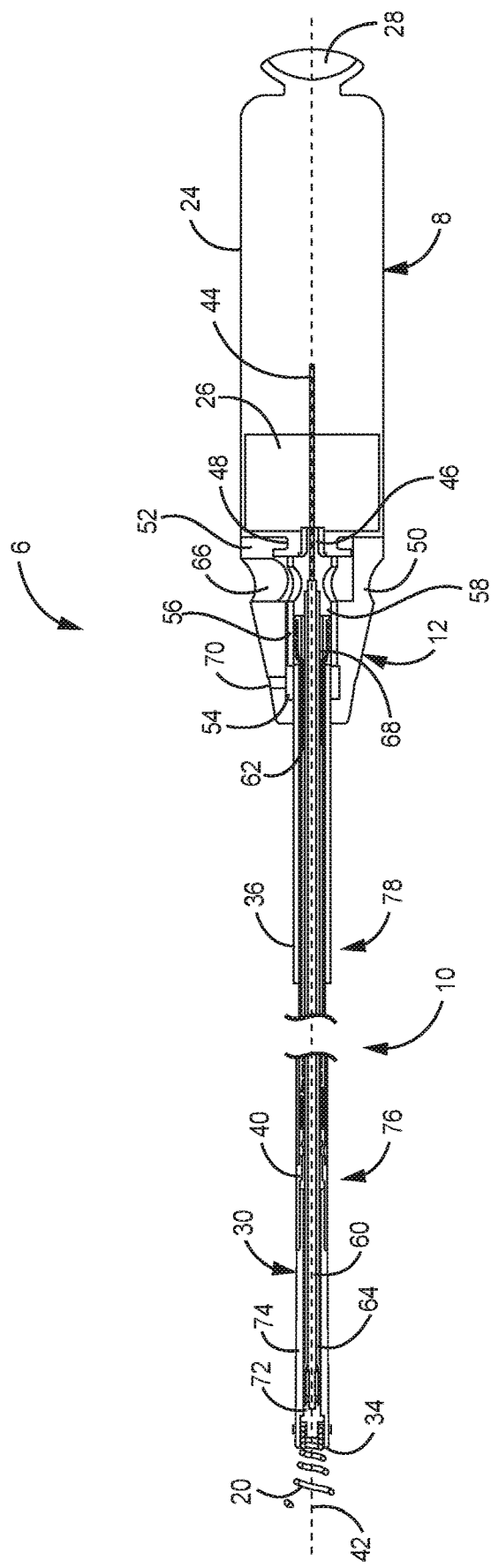
FIG. 3 is a cross-sectional view of the implantable medical device of FIG. 1A, where the cross-section is taken along a plane parallel to a longitudinal axis of the implantable medical device.

FIG. 3 is a cross-sectional view of IMD 6, where the cross-section is taken along a plane parallel to longitudinal axis 42 of IMD 6. IMD 6 further includes an electrically conductive pin 44 positioned to extend from within pulse generator 8, through a distal end of pulse generator 8, and distally of the distal end of pulse generator 8. The conductive pin 44 may be surrounded by glass insulation 46 and, in some cases, form a hermetic feedthrough of housing 24. In some examples, connector segment 12 may help isolate conductive pin 44 from mechanical strain that conductive pin 44 otherwise may undergo when lead 10 is moved relative to pulse generator 8, which may help improve a durability of IMD 6. The distal end of pulse generator 8 further includes one or more connector tabs 48 extending distally of the distal end of pulse generator 8. In some examples, connector tabs 48 may be integrally formed with housing 24 of pulse generator 8. In other examples, connector tabs may be formed separately from housing 24 and attached to housing 24, as described below with respect to FIG. 6. As shown in FIG. 3, connector segment 12 may include a connector segment housing 50. A proximal end of connector segment housing 50 may include one or more connector tabs 52, which may be integrally formed with connector segment 12. Connector tabs 52 of connector segment housing 50 may be configured to engage connector tabs 48 of pulse generator 8. For example, connector tabs 52 may be configured to engage connector tabs 48 by rotation of connector segment 12 about longitudinal axis 42 of lead 10, relative to pulse generator 8, to attach connector segment 12 to pulse generator 8, which may help reduce or prevent movement of connector segment 12 away from pulse generator 8 in a direction of longitudinal axis 42. In such a manner, lead 10 may be securely attached to pulse generator 8 to form IMD 6.

Connector segment housing 50 defines a connector segment lumen 54, which extends from a proximal end of connector segment housing 50 to a distal end of connector segment housing 50. Connector segment 12 further includes an adaptor 56, which defines an adaptor proximal end and an adaptor distal end. Adaptor 56 is configured to be received in connector segment lumen 54, as shown in FIG. 3, and defines an adaptor lumen 58. At the proximal end of adaptor 56, adaptor lumen 58 is configured to receive conductive pin 44. In some examples, elongate body 30 may include a conductive cable 60, which may be configured to operate as first conductor, and a conductive coil 62, which may be configured to operate as a second conductor. In some such examples, conductive pin 44 electrically couples conductive cable 60 to one or more electrical components within housing 24 of pulse generator 8.

Elongate body 30 may further include an insulative layer 64 positioned around an outer surface of conductive cable 60. In some examples, a proximal segment 80 of conductive cable 60 including a proximal end of conductive cable 60 extends proximally of insulative layer 64. When lead 10 is at least partially assembled, fixation helix 20, which may be configured to function as a pace/sense electrode, may be electrically coupled to conductive pin 44 via conductive cable 60. For example, proximal segment 80 of conductive cable 60 and conductive pin 44 both may be positioned within a proximal portion of adaptor lumen 58, thereby electrically coupling fixation helix 20 to conductive pin 44. Electrode 40 may be a pace/sense electrode electrically coupled to a portion of pulse generator 8 around conductive pin 44, via conductive coil 62 and adaptor 56. For example, a proximal segment of conductive coil 62 that includes a proximal end of conductive coil 62 may extend proximally of insulative layer 64. The proximal segment of conductive coil 62 may be positioned within the distal portion of adaptor lumen 58 such that the proximal segment of conductive coil 62 is in contact with adaptor 56. A proximal portion of adaptor 56 may be positioned against a distal end of pulse generator 8, as illustrated in FIG. 3, thereby electrically coupling electrode 40 to pulse generator 8 via conductive coil 62. In some examples, a portion of adaptor 56, such as the proximal portion of adaptor 56, may be welded or otherwise attached to the distal end of pulse generator 8.

Figure 7:
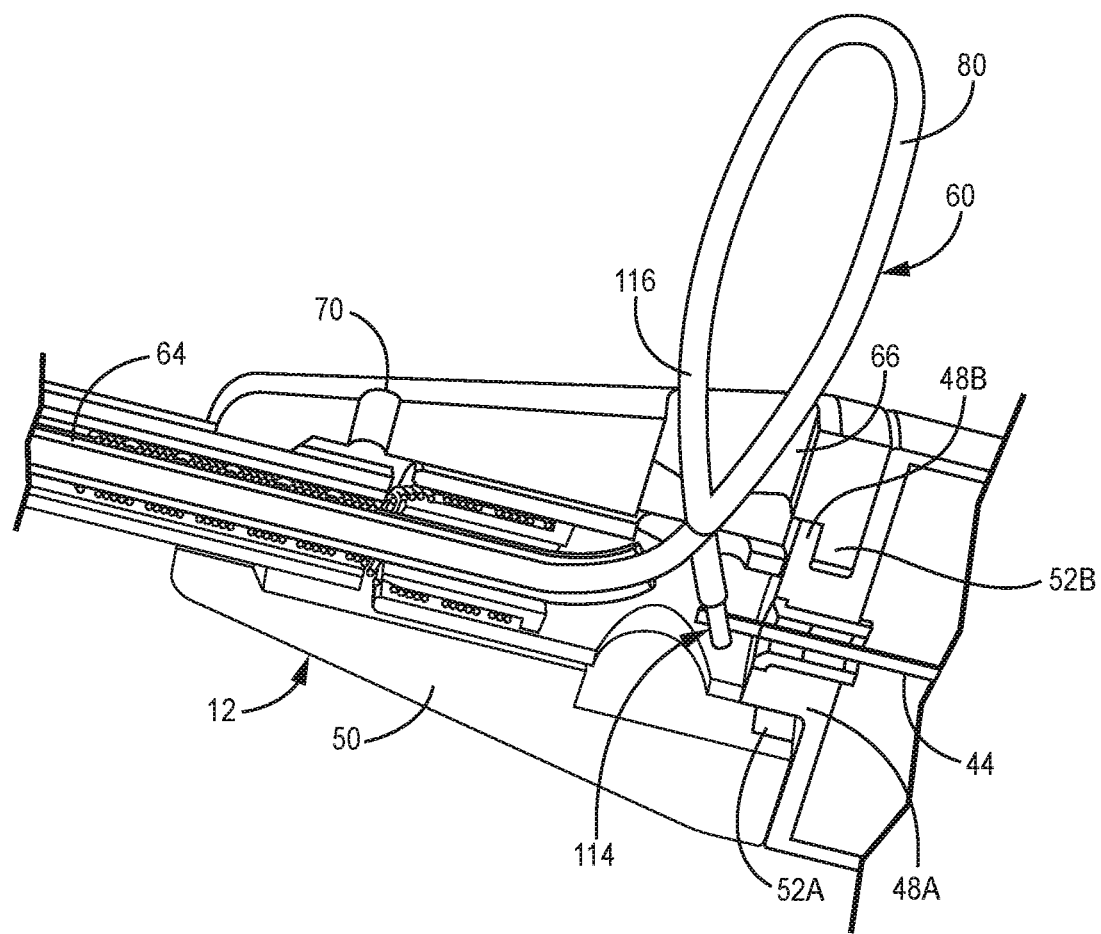
FIG. 7 is a cross-sectional view of a connector segment that includes the adaptor of FIG. 6, where the cross-section is taken along a plane parallel to a longitudinal axis of the lead.

Connector segment housing 50 and adaptor 56 may define a channel 66 extending from an outer surface of connector segment housing 50 radially inward (with respect to connector segment 12) to connector segment lumen 54, and further radially inward to adaptor lumen 58. As illustrated in FIG. 7, a portion of a proximal segment of conductive cable 60 may extend through channel 66 exterior to the outer surface of connector segment 12, such as when the proximal end of conductive cable 60 is received within adaptor lumen 58 and connected to conductive pin 44 during manufacturing of lead 10. In some examples, the portion of the proximal segment of conductive cable 60 that extends through channel 66 exterior during manufacturing of lead 10 may be a length of conductive cable 60 that may be configured to wrap around adaptor 56 to provide strain relief, as further described below with respect to FIG. 7. In some examples, the portion of the proximal segment of conductive cable 60 that is wrapped around adaptor 56 may function as a strain relief segment of conductive cable 60. Such a strain relief segment of conductive cable 60 may reduce a transfer of motion from a distal portion of conductive cable 60 and/or elongate body 30 to conductive cable 60 and/or the connection between conductive cable 60 and conductive pin 44.

For example, the excess length provided by the proximal segment of conductive cable 60 may enable the proximal end of conductive cable 60 to be welded to conductive pin 44 while connector segment housing 50 and pulse generator 8 are spaced apart and some of the proximal segment of conductive cable 60 is received within channel 66. After conductive cable 60 is welded to conductive pin 44, an additional length of the proximal segment of conductive cable 60 may be fed into channel 66, as connector segment housing 50 and pulse generator 8 are brought together and connector tabs 52 of connector segment housing 50 are engaged with connector tabs 48 of pulse generator 8. As connector segment 12 is rotated about longitudinal axis 42 to attach connector segment 12 to pulse generator 8, the rotation may draw the proximal segment of conductive cable 60 radially inward through channel 66 and into connector segment lumen 54, such as by wrapping about adaptor 56 (not shown). For example, about 1-3 turns of the proximal segment of conductive cable 60 may be wrapped about adaptor 56, although additional turns of the proximal segment of conductive cable 60 may be wrapped about adaptor 56 in other examples. In some examples, wrapping the proximal segment of conductive cable 60 about adaptor 56 may help isolate conductive pin 44 from mechanical stress, which may improve the durability of the connection between conductive pin 44 and conductive cable 60 and thus may enhance the durability of IMD 6.

Connector segment 12 may further include a crimp core 68, which may be connected to elongate body 30 near a proximal end of conductive coil 62 and received within adaptor lumen 58. As illustrated in FIG. 3, crimp core 68 may be connected to elongate body 30 such that a proximal portion of conductive coil 62 that extends proximally of strain relief 36 is coiled around crimp core 68. When crimp core 68 is received within adaptor lumen 58, crimp core 68 may hold conductive coil 62 in electrical contact with adaptor 56 and thus in electrical contact with pulse generator 8 when connector segment 12 is connected to pulse generator 8.

Connector segment housing 50 further defines an adhesive fill port 70. Adhesive fill port 70 extends from an outer surface of connector segment housing 50 radially inward to connector segment lumen 54. During manufacturing of IMD 6, adhesive may be introduced into adhesive fill port 70 after connector segment 12 has been connected to pulse generator 8 and the proximal portion of conductive cable 60 drawn into connector segment lumen 54 and wrapped about adaptor 56. Introduction of adhesive into connector segment lumen 54 via adhesive fill port 70 may cause the adhesive to fill in voids within connector segment lumen 54 not occupied by adaptor 56 or other components of lead 10, which may help secure the positions of the components of lead 10 positioned within connector segment lumen 54 and thus improve the mechanical integrity and electrical coupling of the components of IMD 6. In some examples, the adhesive may isolate components of IMD 6 from fluids that may short electrical conductors of IMD 6 and/or degrade glass insulation 46.

Lead 10 may further include a weld core 72 comprising a conductive material connected to a distal end of conductive cable 60. A proximal portion of weld core 72 may define a lumen configured to receive the distal end of conductive cable 60, and a distal end of weld core 72 may be configured to be received within a proximal end of fixation helix 20, as illustrated in FIG. 3, such that fixation helix 20 is electrically coupled to conductive cable 60. Conductive cable 60, weld core 72, and fixation helix 20 may be retained in contact and insulated by a distal sleeve 74, which may be made of polyurethane or another suitable insulative material. Distal sleeve 74 may be positioned around fixation helix 20, weld core 72, and a portion of conductive cable 60 distal to electrode 40.

Electrode 40 is illustrated in FIG. 3 as being an elongate ring electrode positioned around insulative layer 64. In some examples, electrode 40 may have a length between about 0.1 cm and about 1.0 cm. Electrode 40 may have other configurations than that of a ring electrode. For example, electrode 40 may be a flat ribbon electrode, paddle electrode, braided or woven electrode, mesh electrode, segmented electrode, directional electrode, patch electrode or other type of electrode positionable on elongate body 30. In some examples, elongate body 30 may include more than one electrode 40. In such examples, each of the electrodes 40 may be spaced axially from one another relative to longitudinal axis 42 of lead 10 and electrically coupled to pulse generator 8 via adaptor 56. In other examples, lead 10 may include a single pace/sense electrode or more than two pace/sense electrodes.

In some examples, electrode 40 may be shaped, oriented, designed or otherwise configured to reduce extracardiac stimulation. For example, electrode 40 may be shaped, oriented, designed or otherwise configured to focus, direct or point electrode 40 toward heart 14. In this manner, pacing pulses delivered via lead 10 are directed toward heart 14 and not outward toward non-cardiac tissue. For example, electrode 40 may be partially coated or masked with a polymer (e.g., polyurethane) or another coating material (e.g., tantalum pentoxide) on one side or in different regions so as to direct the pacing signal toward heart 14 and not outward toward non-cardiac tissue.

IMD 6 may obtain sensed electrical signals corresponding with electrical activity of heart 14 via a combination of sensing vectors that include combinations of fixation helix 20, electrode 40, and housing electrode 26. For example, IMD 6 may obtain electrical signals sensed using a sensing vector between fixation helix 20 and electrode 40, obtain electrical signals sensed using a sensing vector between fixation helix 20 and housing electrode 26, obtain electrical signals sensed using a sensing vector between electrode 40 and the housing electrode 26, or a combination thereof.

IMD 6 analyzes the sensed electrical signals obtained from one or more of the sensing vectors of lead 10 and/or pulse generator 8 to monitor for bradycardia. In response to detecting bradycardia, IMD 6 may be configured to generate and deliver bradycardia pacing via a pacing vector. In some such examples, the pacing vector may be a pacing vector between fixation helix 20 and electrode 40, a pacing vector between fixation helix 20 and housing electrode 26, a pacing vector between electrode 40 and the housing electrode 26, or a combination thereof. In other examples, IMD 6 may analyze the sensed electrical signals to monitor for tachyarrhythmia, such as ventricular tachycardia (VT) or ventricular fibrillation (VF). In such examples, IMD 6 may be configured to generate and deliver cardiac pacing (e.g., ATP and/or post-shock pacing) in response to detecting tachyarrhythmia. In some examples, IMD 6 may be configured to generate and deliver cardiac resynchronization therapy (CRT) in addition to or instead of bradycardia pacing, ATP, and/or post-shock pacing.

Figure 4:
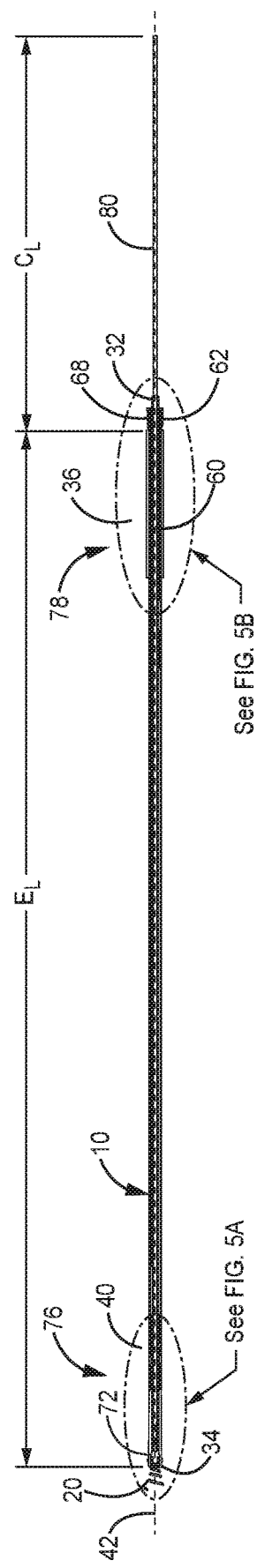
FIG. 4 is a cross-sectional view of the lead of the implantable medical device of FIG. 1A, where the cross-section is taken along a plane parallel to a longitudinal axis of the lead and a proximal portion and a distal portion of the lead are outlined.

FIG. 4 is a cross-sectional view of lead 10, where the cross-section is taken along a plane parallel to longitudinal axis 42 of lead 10. Lead 10 includes a distal portion 76 and a proximal portion 78, which are outlined in FIG. 4. Distal portion 76 of lead 10, which includes fixation helix 20, electrode 40, and weld core 72, is further discussed below with respect to FIG. 5A. Proximal portion 78 of lead 10, which includes strain relief 36, conductive cable 60, conductive coil 62, and crimp core 68, is further discussed below with respect to FIG. 5B.

As illustrated in FIG. 4, elongate body 30 of lead 10, which extends from proximal end 32 of elongate body 30 to distal end 34 of elongate body 30, may have a length $E_L$, which may be from about 5 cm to about 25 cm. A proximal portion 80 of conductive cable 60, which may be wrapped about adaptor 56 when IMD 6 is assembled, as discussed above with respect to FIG. 3, may have a length $C_L$. In some examples, length $C_L$ may be from about 2 cm to about 6 cm. In some other examples, EL and/or CL may have other values, such as based on the anatomy of patient 4 or one or more dimensions of other components of IMD 6.

Figure 5A:
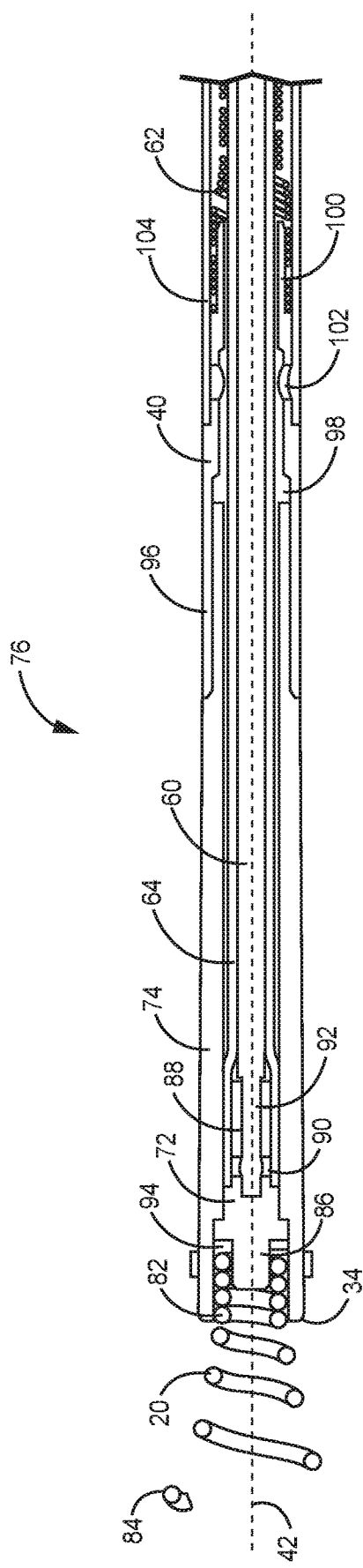
FIG. 5A is a cross-sectional view of the distal portion of the lead outlined in FIG. 4, where the cross-section is taken along a plane parallel to a longitudinal axis of the lead.

FIG. 5A is a cross-sectional view of distal portion 76 of lead 10 as outlined in FIG. 4, where the cross-section is taken along a plane parallel to longitudinal axis 42 of lead 10. As illustrated in FIG. 5A, fixation helix 20 defines a proximal end 82 and a distal end 84. Weld core 72 includes a tab 86 at a distal portion of weld core 72 and defines a weld core lumen 88 at a proximal portion of weld core 72. Weld core 72 is configured to electrically couple fixation helix 20 to conductive cable 60. For example, tab 86 is configured to be received within proximal end 82 of fixation helix 20. Fixation helix 20 and weld core 72 then may be secured to one another, such as by welding. Conductive cable 60 includes a distal portion 92. Distal portion 92 of conductive cable 60 may be stripped of an insulative coating (described in further detail with respect to FIG. 7) to electrically couple conductive cable 60 to weld core 72.

Weld core 72 further defines an adhesive fill port 90. Adhesive fill port 90 extends from an outer surface of weld core 72 radially inward to weld core lumen 88. During manufacturing of lead 10, adhesive may be introduced into adhesive fill port 90 after distal portion 92 of conductive cable 60 is received within weld core lumen 88 as illustrated in FIG. 5A. Introduction of adhesive into connector segment lumen 54 via adhesive fill port 70 may cause the adhesive to fill in voids within weld core lumen 88 not occupied by distal portion 92 of conductive cable 60, which may help secure distal portion 90 weld core lumen 88 and thus improve the mechanical integrity and electrical coupling of the components of lead 10.

After distal portion 92 of conductive cable 60 is received within weld core lumen and the adhesive is introduced into adhesive fill port 90, insulative layer 64 may be positioned around conductive cable 60 and a proximal portion of weld core 72. Distal sleeve 74 defines a lumen 94, which may be configured to receive proximal end 82 of fixation helix 20, weld core 72, insulative layer 64, and conductive cable 60. Thus, after fixation helix 20, weld core 72, insulative layer 64, and conductive cable 60 are assembled as illustrated in FIG. 5A, distal sleeve 74 may be positioned over said components. Distal sleeve 74 may provide electrical insulation for portions of weld core 72 not received within insulative layer 64 and for proximal end 82 of fixation helix 20.

Fixation helix 20 may have a width at proximal end 82 that is less than a width of distal end 84 of fixation helix 20. For example, proximal end 82 of fixation helix 20 may have a width of about 0.08 cm to about 0.20 cm. In addition, the width of fixation helix 20 at distal end 84 is greater than a width of distal sleeve 74 at distal end 34 of elongate body 30. As discussed above, elongate body 30 may have a width $E_W$, which may be from about 0.06 cm (about 2 French (Fr)) to about 0.19 (cm) (about 6 French), such as at distal end 34. Thus, distal end 84 of fixation helix 20 may have a width that is greater than the width of distal end 34 of elongate body 30, which may be in a ratio of about 3:2 to about 4:1.

The configuration of distal end 84 of fixation helix 20 may provide one or more advantages. For example, the relatively greater width of distal end 84 of fixation helix 20 may enable lead 10 to be attached to the epicardium of heart 14 with fixation helix 20 and/or at least a portion of elongate body 30 positioned substantially parallel to the epicardium of heart 14 and to pericardium 22. For example, the relatively greater width of distal end 84 may reduce a possibility of elongate body 30 interfering with contact between distal end 84 of fixation helix 20 and the epicardium of heart 14 when elongate body 30 is substantially parallel to the epicardium of heart 14. In some examples, enabling lead 10 to be attached to the epicardium of heart 14 with fixation helix 20 and/or at least a portion of elongate body 30 substantially parallel to the epicardium of heart 14 and to pericardium 22, which may reduce a possibility of deformation of the epicardium of heart 14 and/or of pericardium 22.

For example, such an attachment of lead 10 to the epicardium of heart 14 may help reduce bending of elongate body 30 away from the epicardium of heart 14, which may reduce an amount of force exerted on the epicardium by fixation helix 20 and/or reduce an amount of force exerted on pericardium 22 by a portion of elongate body 30 proximal to distal end 34. By reducing an amount of force exerted on the epicardium of heart 14 and/or pericardium 22 by one or more portions of lead 10, the configuration of fixation helix 20 may reduce indentation or other deformation of the epicardium of heart 14 and/or pericardium 22.

In some examples, such an attachment of lead 10 to the epicardium of heart 14 may help facilitate a lead implantation procedure. For example, attachment of lead 10 to the epicardium of heart 14 may be achieved using a straight delivery catheter, which may be easier for a clinician to manipulate and reposition as needed than a bent delivery catheter (e.g., such as may be needed to accommodate a lead bending outwardly away from the epicardium of heart 14 during a lead implantation procedure). The substantially parallel placement of at least a portion of lead 10 that includes fixation helix 20 and/or at least a portion of elongate body 30 to the epicardium of heart 14 and pericardium 22 may reduce friction of lead 10 within a delivery catheter relative to lead placements in which a lead is bend outwardly away from the epicardium of heart 14 during a lead implantation procedure, and/or may reduce an amount of torque that a clinician may need to apply to lead 10 while rotating lead to cause fixation helix 20 to engage with the epicardium of heart 14. In this manner, the configuration of fixation helix 20 may help facilitate a procedure in which the clinician may implant lead 10 within patient 4, which may reduce a length of time needed to complete the procedure.

Additionally, or alternatively, the attachment of lead 10 to the epicardium of heart 14 such that fixation helix 20 and/or a portion of elongate body 30 substantially parallel to the epicardium of heart 14 and to pericardium 22 may help maintain electrode 40 in contact with or in close proximity to the epicardium of heart 14. As discussed above with respect to FIG. 1A, contact or close proximity of electrode 40 to the epicardium of heart 14 may help reduce a pacing threshold and/or may reduce power consumption of IMD 6. In some examples, elongate body 30 may be flexible, which may help enable lead 10 to conform to the shape of heart 14 and maintain electrode 40 in contact with or in close proximity to the epicardium of heart 14.

In some examples, fixation helix 20 may have a length of about 0.2 cm to about 1.2 cm, and may have a pitch of about 0.06 to about 0.20. In some examples, a pitch of fixation helix 20 may be greater at distal end 84 than at a proximal portion of fixation helix 20. The length and/or pitch of fixation helix 20 may enable fixation helix 20 to engage the epicardium of heart 14 for about 3 full turns, which may help fixation helix 20 to securely attach to the epicardium. In other examples, a length and/or a pitch of fixation helix 20 may vary, such that fixation helix 20 may be configured to engage the epicardium of heart 14 for any suitable number of turns. In some examples, a distal tip of fixation helix 20 at distal end 84 may be pointed, which may help enable fixation helix 20 to pierce and be advanced through the epicardium of heart 14.

Electrode 40 is positioned around insulative layer 64 and includes a distal portion 96. Distal portion 96 of electrode 40 defines an electrode lumen 98, which may be configured to receive a proximal portion of distal sleeve 74 such that electrode 40 is electrically insulated from weld core 72, conductive cable 60, and fixation helix 20. Electrode 40 further includes a proximal portion 100 and an adhesive fill port 102. Conductive coil 62 is positioned around proximal portion 100 of electrode 40 and may be configured to electrically couple electrode 40 to a portion of pulse generator 8 around conductive pin 44 via adaptor 56. During assembly of lead 10, distal portion 96 of electrode 40 may be positioned over distal sleeve 74 such that distal sleeve 74 is received within electrode lumen 98, and proximal portion 100 of electrode 40 may be positioned within conductive coil 62. Adhesive may be introduced into electrode lumen 98 via adhesive fill port 102 after electrode 40 has been connected to distal sleeve 74 and conductive coil 62. Introduction of adhesive into electrode lumen 98 via adhesive fill port 102 may cause the adhesive to fill in voids within electrode lumen 98 not occupied by distal sleeve 74 or other components of elongate body 30, which may help secure the positions of the components of elongate body 30 positioned within electrode lumen 98 via mechanical bonding of such components, and thus may improve the mechanical integrity and electrical coupling of the components of elongate body 30 at electrode 40.

In some examples, elongate body 30 further includes a proximal sleeve 104, which is positioned over proximal portion 100 of electrode 40 and conductive coil 62. Proximal sleeve 104 may be made of a non-conductive, flexible material, such as silicone, polyurethane, or any other suitable material. An outer surface of electrode 40 distal to proximal portion 100 of electrode 40 is exposed on an outer surface of elongate body 30, enabling electrode 40 to sense electrical signals from heart 14 and/or deliver electrical stimulation (e.g., cardiac pacing) to heart 14.

Figure 5B:
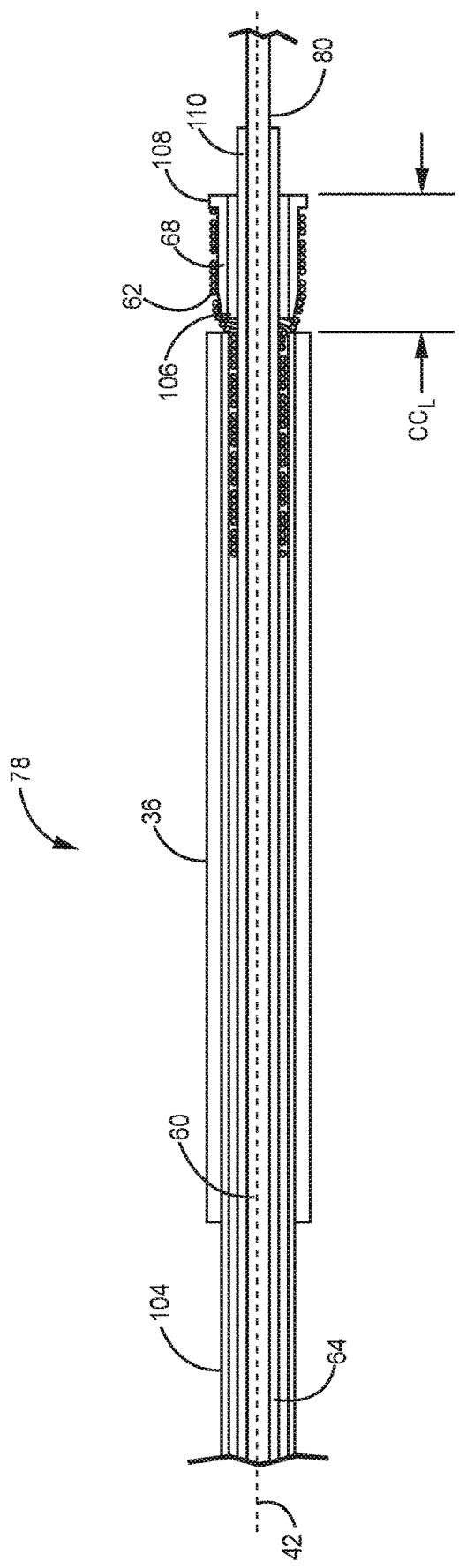
FIG. 5B is a cross-sectional view of the proximal portion of the lead outlined in FIG. 4, where the cross-section is taken along a plane parallel to a longitudinal axis of the lead.

FIG. 5B is a cross-sectional view of the proximal portion of the lead outlined in FIG. 4, where the cross-section is taken along a plane parallel to longitudinal axis 42 of lead 10. As illustrated in FIG. 5B, crimp core 68 defines a distal end 106 and a proximal end 108. Insulative layer 64 defines a proximal portion 110 that extends proximally of the proximal end of crimp core 68. Proximal portion 80 of conductive cable 60 may extend proximally of proximal portion 110 of insulative layer 64 and proximally of proximal end 108 of crimp core 68. Crimp core 68 may have a length CCL, which may be from about 0.2 cm to about 1.0 cm.

Figure 6:
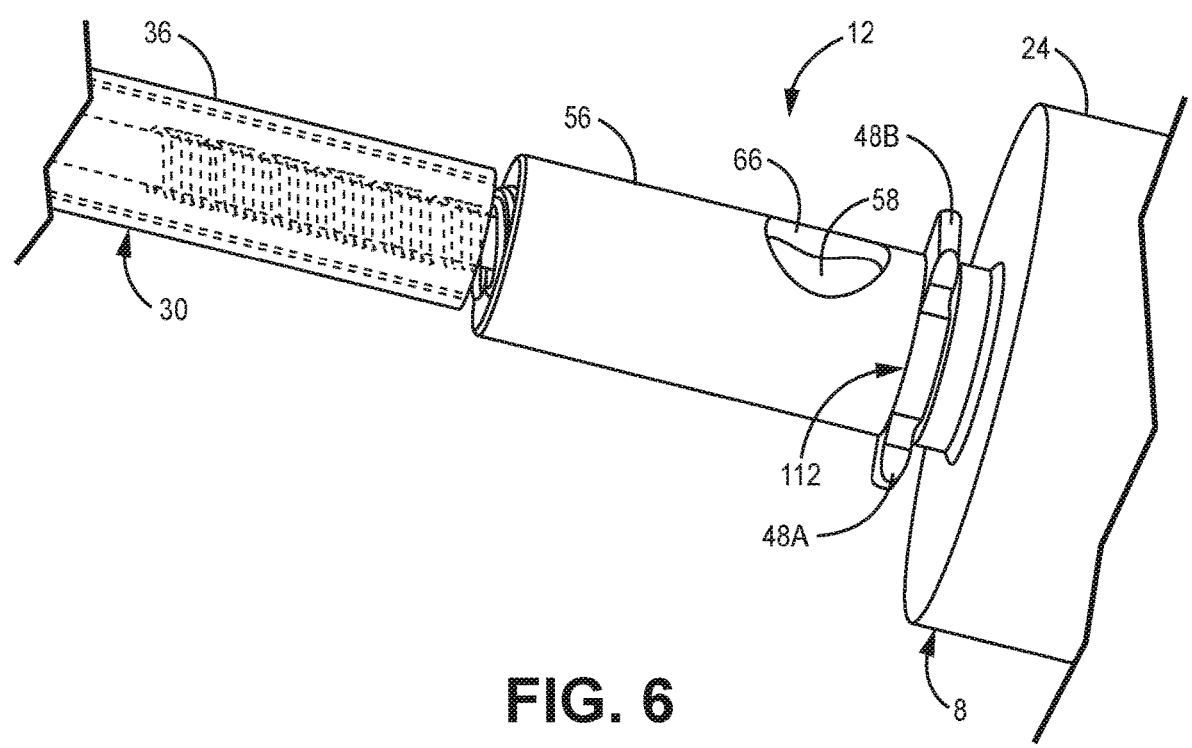
FIG. 6 is a side view of an adaptor connecting the lead of the implantable medical device of FIG. 1A to the pulse generator of the implantable medical device of FIG. 1A.

FIG. 6 is a side view of adaptor 56 connecting elongate body 30 to pulse generator 8 of IMD 6. As illustrated in FIG. 6, pulse generator 8 may include an endcap 112 positioned at a distal end of housing 24. Endcap 112 is formed from an electrically conductive material (e.g., a same material as a material from which housing 24 is formed) and may be welded to the distal end of housing 24. Thus, electrode 40 and conductive coil 62 may be electrically coupled to housing 24 via endcap 112.

Endcap 112 includes connector tabs 48, which may include a first connector tab 48A and a second connector tab 48B. Endcap 112 may further include a third connector tab (not shown). In some examples, the third connector tab may be positioned between first and second connector tabs 48A, 48B (e.g., about longitudinal axis 42 of IMD 6) such that connector tabs 48 are substantially equidistant from one another about longitudinal axis 42. In other examples, connector tabs 48 may be positioned on endcap 112 such that connector tabs 48 are not substantially equidistant from one another, and/or endcap 112 may include one or more additional connector tabs 48 or a single connector tab 48.

FIG. 7 is a cross-sectional view of a connector segment 12 that includes adaptor 56, where the cross-section is taken along a plane parallel to a longitudinal axis 42 of lead 10. FIG. 7 further illustrates the connection between conductive cable 60 and conductive pin 44 during assembly of IMD 6. Conductive cable 60 further includes a conductive core 114 and an insulative coating 116 surrounding conductive core 114. As illustrated in FIG. 7, a length of conductive core 114 may be devoid of insulative coating 116 at a proximal end of conductive core 114 to enable electrical coupling (e.g., welding) of conductive cable 60 to conductive pin 44. For example, a portion of conductive core 114 having a length of about 0.07 cm to about 1.0 cm may be devoid of insulative coating 116 at a proximal end of conductive core 114. However, a length of conductive core 114 that is devoid of insulative coating 116 at a proximal end of conductive core 114 may vary in other examples, such as based on a size of one or more components of IMD 6, a desired weld strength, manufacturing equipment being used to assemble IMD 6, and/or other factors.

FIG. 7 also further illustrates the connection between connector tabs 52 of connector segment housing 50 and connector tabs 48 of pulse generator 8 during assembly of IMD 6. In some examples, connector tabs 52 may include a first connector tab 52A and a second connector tab 52B. Connector tabs 52 may further include a third connector tab (not shown). Connector segment housing 50 may further include a third connector tab (not shown). In some examples, the third connector tab may be positioned between first and second connector tabs 52A, 52B (e.g., about longitudinal axis 42 of IMD 6) such that connector tabs 52 are spaced substantially equidistant from one another about longitudinal axis 42. In other examples, connector tabs 52 may be positioned on connector segment housing 50 such that connector tabs 52 are not spaced substantially equidistant from one another, and/or connector segment housing 50 may include one or more additional connector tabs 52. In any such examples, connecter segment housing 50 may include a same number of connector tabs 52 as a number of connector tabs 48 of pulse generator 8, such that connector tabs 52 may engage connector tabs 48 in a 1:1 ratio when connector segment 12 is attached to pulse generator 8. As illustrated in FIG. 7, connector tabs 52 and connector tabs 48 may have complementary shapes, such that each one of connector tabs 52 interlocks with a corresponding one of connector tabs 48.

For example, each of connector tabs 48 and each of connector tabs 52 may be configured to pass through spaces between others of connector tabs 48 and connector tabs 52 when a proximal end of connector segment 12 is positioned to engage connector tabs 52 and connector tabs 48, such as during an example technique for manufacturing IMD 6. With the proximal end of connector segment 12 so positioned, rotation of connector segment 12 about longitudinal axis 42 of lead 10 relative to pulse generator 8 may cause connector tabs 52 and connector tabs 48 to interlock with one another. For example, rotation of connector segment 12 about longitudinal axis 42 of lead 10 relative to pulse generator 8 may cause connector tabs 52 to slide under respective ones of connector tabs 48, as illustrated in FIG. 7.

Figure 8:
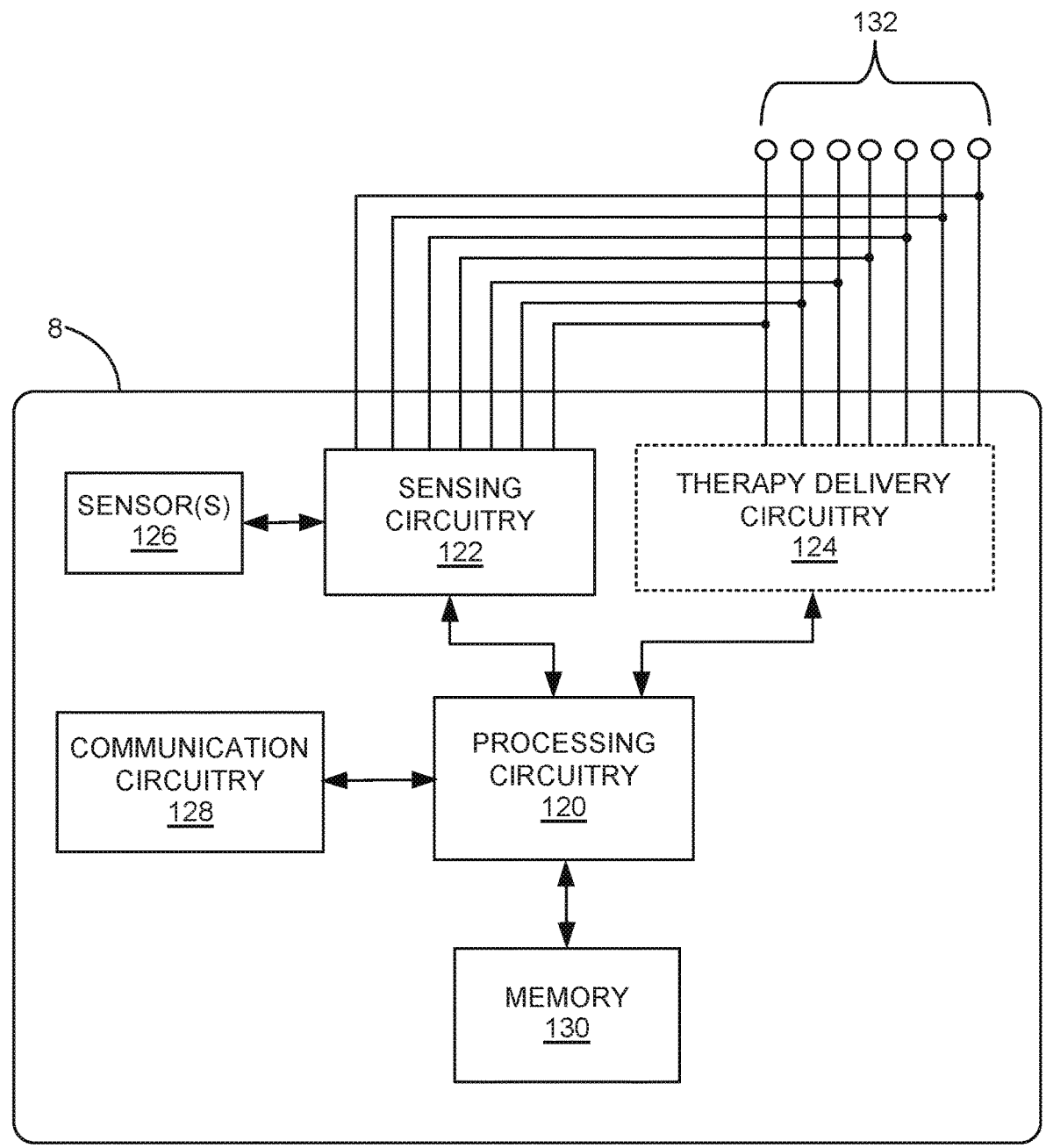
FIG. 8 is a functional block diagram illustrating an example configuration of the implantable medical device of FIG. 1A.

FIG. 8 is a functional block diagram illustrating an example configuration of pulse generator 8 of IMD 6. As shown in FIG. 8, IMD 6 includes processing circuitry 120, sensing circuitry 122, therapy delivery circuitry 124, sensors 126, communication circuitry 128, and memory 130. In addition, IMD 6 includes one or more electrodes 132, which may be any one or more of fixation helix 20, electrode 40, housing electrode 26, and/or any other electrodes positioned on lead 10 or pulse generator 8. In some examples, memory 130 includes computer-readable instructions that, when executed by processing circuitry 120, cause IMD 6 and processing circuitry 120 to perform various functions attributed to IMD 6 and processing circuitry 120 herein. Memory 130 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 120 may include fixed function circuitry and/or programmable processing circuitry. Processing circuitry 120 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 120 may include multiple components, such as any combination of one or more microprocessors, one or more controllers, one or more DSPs, one or more ASICs, or one or more FPGAs, as well as other discrete or integrated logic circuitry. The functions attributed to processing circuitry 120 herein may be embodied as software, firmware, hardware or any combination thereof.

In some examples, processing circuitry 120 may receive (e.g., from external device 18), via communication circuitry 128, a respective value for each of a plurality of cardiac sensing parameters, cardiac therapy parameters (e.g., cardiac pacing parameters), and/or electrode vectors. Processing circuitry 120 may store such parameters and/or electrode vectors in memory 130.

Therapy delivery circuitry 124 and sensing circuitry 122 are electrically coupled to electrodes 132, which may include one or more of electrodes 132. Processing circuitry 120 is configured to control therapy delivery circuitry 124 to generate and deliver electrical stimulation to heart 14 via electrodes 132. Electrical stimulation may include, for example, pacing pulses, or any other suitable electrical stimulation. Processing circuitry 120 may control therapy delivery circuitry 124 to deliver electrical stimulation therapy via electrodes 132 according to one or more therapy programs including pacing instructions that define a pacing rate, which may be stored in memory 130.

In addition, processing circuitry 120 is configured to control sensing circuitry 122 to monitor signals from electrodes 132 in order to monitor electrical activity of heart 14. Sensing circuitry 122 may include circuits that acquire electrical signals. Sensing circuitry 122 may acquire electrical signals from a subset of electrodes 132. Electrical signals acquired by sensing circuitry 122 may include intrinsic and/or paced cardiac electrical activity, such as atrial depolarization and/or ventricular depolarization. Sensing circuitry 122 may filter, amplify, and digitize the acquired electrical signals to generate raw digital data. Processing circuitry 120 may receive the digitized data generated by sensing circuitry 122. In some examples, processing circuitry 120 may perform various digital signal processing operations on the raw data, such as digital filtering.

In some examples, in addition to sensing circuitry 122, IMD 6 optionally may include sensors 126, which may comprise at least one of a variety of different sensors. For example, sensors 126 may comprise one or more pressure sensors and/or one or more accelerometers. Sensors 126 may detect signals associated with one or more physiological parameters of patient 4, such as an activity level, a hemodynamic pressure, and/or heart sounds. Processing circuitry 120 may use signal detected by sensors 126 to adapt one or more cardiac pacing parameters, such as by increasing a rate of delivery of pacing pulses in response to detecting an increase in patient 4's activity level.

Communication circuitry 128 may include any suitable hardware (e.g., an antenna), firmware, software, or any combination thereof for communicating with another device, such as external device 18 or a patient monitor. Under the control of processing circuitry 120, communication circuitry 128 may receive downlink telemetry from and send uplink telemetry to other devices (e.g., external device 18) such as via an antenna included in communication circuitry 128.

Figure 9:
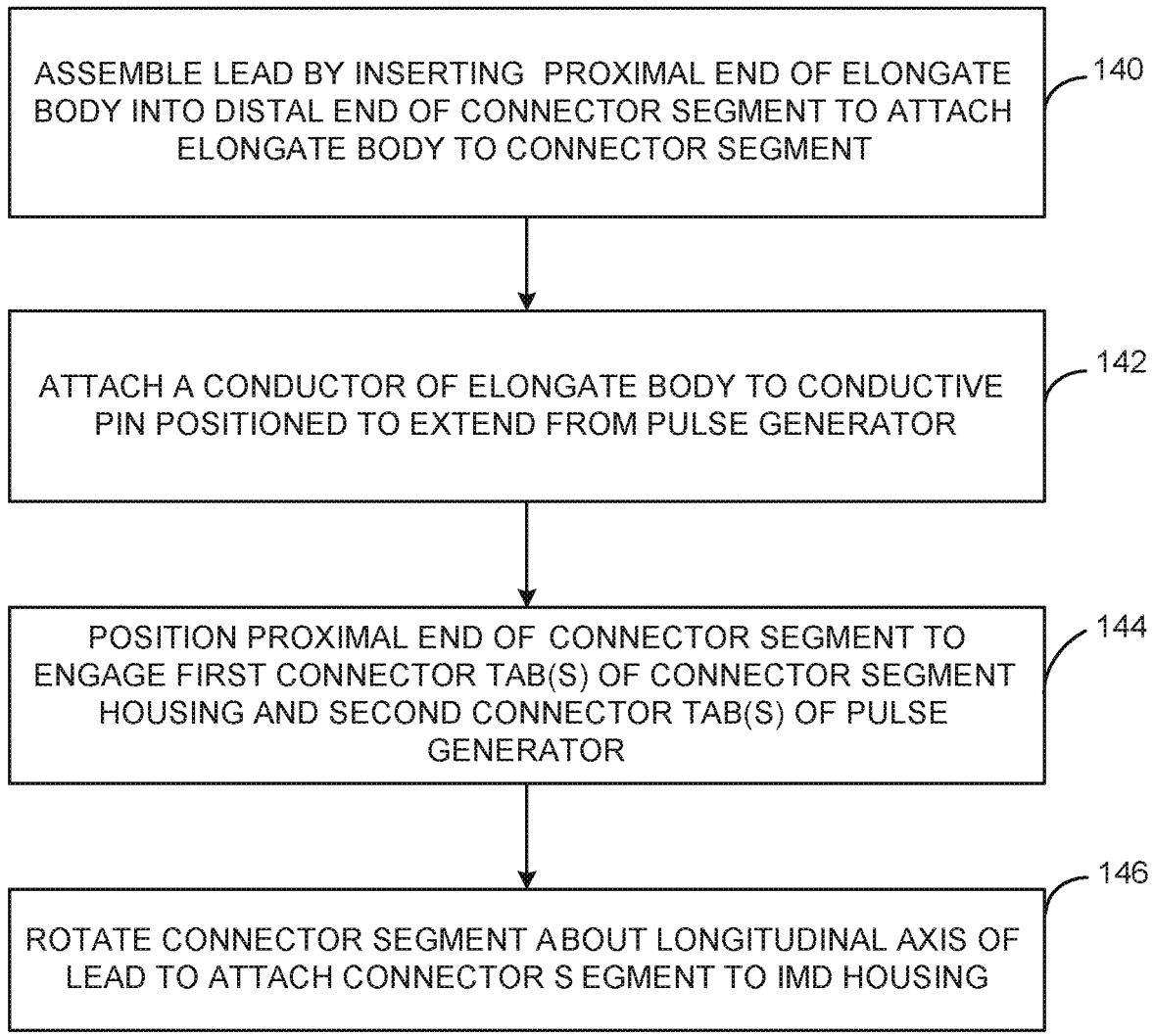
FIG. 9 is a flow diagram illustrating an example technique for manufacturing an implantable medical device.

FIG. 9 is a flow diagram illustrating an example technique for manufacturing IMD 6. Although the example technique of FIG. 9 is described in the context of IMD 6, the example technique should not be understood to be so limited, but instead may be applied to the manufacture of other example IMDs within the scope of this disclosure.

The example technique of FIG. 9 includes assembling lead 10 (140). Assembling lead 10 includes attaching elongate body 30 to connector segment 12 such that a portion of elongate body proximal to strain relief 36 and distal to proximal end 32 is received within adaptor lumen 58 of adaptor 56. Assembling lead 10 may further include positioning crimp core 68 around the portion of elongate body proximal to strain relief 36 and distal to proximal end 32 of elongate body 30 prior to inserting the proximal end of elongate body 30 into adaptor lumen 58. In some examples, assembling lead 10 also may include attaching fixation helix 20 to distal end 34 of elongate body 30. Attaching elongate body 30 to the connector segment may further include inserting crimp core 68 into adaptor lumen 58 at a distal end of adaptor 56.

Next, elongate body 30 may be attached to conductive pin 44 (142). For example, elongate body 30 may be attached to conductive pin 44 by welding a proximal end of conductive core 114 of conductive cable 60 (e.g., a portion of conductive core 114 devoid of insulative coating 116) to conductive pin 44. Attaching conductive cable 60 to conductive pin 44 electrically couples fixation helix 20 to conductive pin 44 via the conductive cable 60.

Next, the proximal end of connector segment 12 may be positioned to engage connector tabs 52 of connector segment housing 50 and connector tabs 48 of pulse generator 8 (144). With connector segment 12 and pulse generator 8 so positioned, connector segment 12 and pulse generator 8 may be attached to one another by rotating connector segment 12 about longitudinal axis 42 of lead 10 relative to pulse generator 8. Rotating connector segment 12 about longitudinal axis 42 of lead 10 relative to pulse generator 8 may cause connector tabs 52 and connector tabs 48 to interlock with one another, thus attaching lead 10 to pulse generator 8 via connector segment 12 (146). Attaching connector segment 12 to pulse generator 8 also may draw proximal portion 80 of conductive cable 60, which may have been extending through channel 66 during welding of the proximal end of conductive core 114 to conductive pin 44) into channel 66, such that proximal portion 80 of conductive cable 60 wraps about adaptor 56. Wrapping proximal segment 80 of conductive cable 60 about adaptor 56 may help isolate conductive pin 44 from mechanical stress, which may improve the durability of the connection between conductive pin 44 and conductive cable 60.

In some examples, assembling IMD 6 may further include introducing an adhesive into adhesive fill port 70 defined by connector segment housing 50 after attaching connector segment 12 to pulse generator 8 such that the adhesive is introduced into connector segment lumen 54. Filling voids within connector segment lumen 54 not occupied by adaptor 56 or other components of lead 10, such as by introducing the adhesive via adhesive fill port 70, may help secure the positions of the components of lead 10 positioned within connector segment lumen 54, which may improve the mechanical integrity and/or the electrical coupling of the components of IMD 6.

Figure 10:
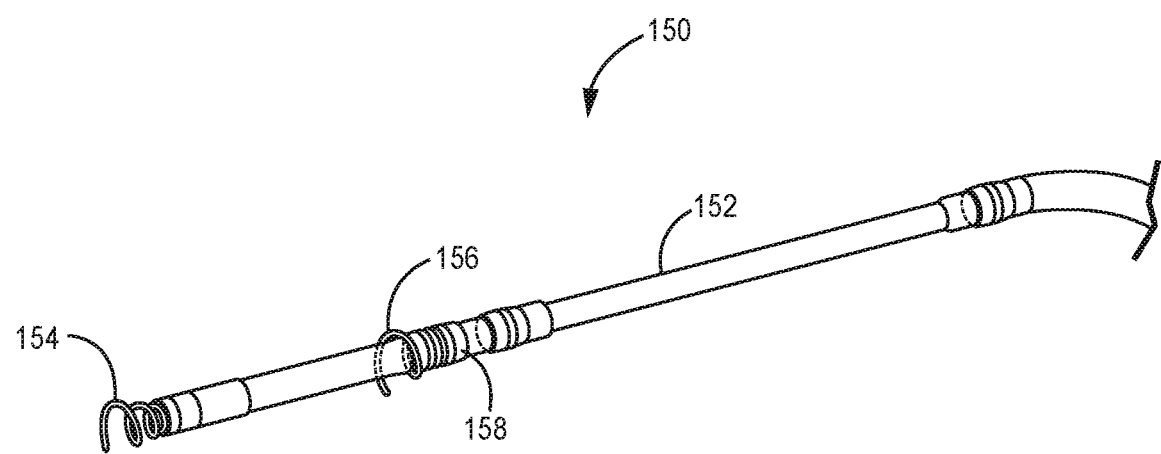
FIG. 10 is a side view of another example lead having multiple fixation helices.

FIG. 10 is a side view of another example lead 150. In some examples, one or more components of lead 150 may be substantially similar to one or more corresponding components of lead 10 as described above with respect to FIGS. 1A-9. For example, lead 150 may include an elongate body 152 that may be substantially similar to elongate body 30. Lead 150 also may include a fixation helix 154 attached to a distal end of elongate body 152. One or more aspects of fixation helix 154 may be substantially similar to those of fixation helix 20, such one or more dimensions or other aspects of a configuration of fixation helix 154. In addition to fixation helix 154, elongate body 152 further includes a fixation helix 156 positioned proximal to fixation helix 154 and extending around an outer surface of elongate body 152.

As with fixation helix 154, a width of fixation helix 156 may be greatest at a distal end of fixation helix 156, although the width of fixation helix 156 may or may not have a substantially continuous taper. The greatest width of fixation helix 156 also may be substantially greater than a width of elongate body 152, such that a distal portion of fixation helix 156 extends outwardly from the outer surface of elongate body 152. The distal portion of fixation helix 156 may extend outwardly from the outer surface of elongate body 152 for approximately 1.5 turns. In some examples, the configuration of fixation helix 156 may help enable fixation helix 156 to engage with cardiac tissue of heart 14 (e.g., the epicardium of heart 14) when at least a portion of lead 150 that includes fixation helix 156 and/or a portion of elongate body 152 that includes one or more electrodes is positioned substantially parallel to the epicardium of heart 14 and to pericardium 22.

In some examples, fixation helix 156 may provide one or more advantages to the configuration and/or use of lead 150.

For example, fixation helix 156 may reduce or substantially eliminate a pivot point in lead 150 that may occur when lead 150 is attached to epicardium of heart 14, such as at a portion of elongate body 152 between the distal and proximal ends thereof. Reducing or eliminating a pivot point in lead 150 may help reduce movement of lead 150 and may help stabilize lead 150 relative to heart 14. In some examples, stabilizing lead 150 relative to heart 14 may help stabilize magnitude of pacing pulses needed to achieve pacing capture of heart 14, which may help IMD 6 consistently achieve pacing capture of heart 14.

Additionally, or alternatively, fixation helix 156 may help maintain one or more electrodes positioned along lead 150 in contact with, or in close proximity to, the epicardium of heart 14. For example, lead 150 may include one or more electrodes 158 positioned along a length of elongate body 152 between the distal and proximal ends of elongate body 152. Fixation helix 156 may be positioned near one or more of electrodes 158 and thus may help maintain electrodes 158 in contact with, or in close proximity to, the epicardium of heart 14, which may help reduce a threshold magnitude of pacing pulses needed to achieve pacing capture of heart 14. In some examples, lead 150 may include one or more additional fixation helices, which may be positioned on elongate body 152 proximal to or distal to fixation helix 156, such as in examples in which lead 150 includes multiple electrodes 158.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. An implantable medical device comprising:
    a pulse generator defining a proximal end and a distal end and comprising a housing;
    a plurality of electrodes;
    circuitry within the housing, the circuitry configured to deliver cardiac pacing via the electrodes; and
    a lead defining a longitudinal axis, wherein the lead comprises at least one of the electrodes, the lead further comprising:
        an elongate body defining a proximal end and a distal end, wherein the proximal end of the elongate body is connected to the distal end of the housing; and
        a first fixation helix attached to the distal end of the elongate body and defining a proximal end and a distal end, wherein a width of the first fixation helix transverse to the longitudinal axis is greatest at the distal end of the fixation helix;
        a second fixation helix extending around the elongate body and positioned between the proximal end of the elongate body and the distal end of the elongate body, the second fixation helix comprising a proximal end and a distal end, and wherein the proximal end of the second fixation helix has a first pitch and the distal end of the second fixation helix has a second pitch that is greater than the first pitch.

2. The device of claim 1, wherein the first fixation helix is configured to engage cardiac tissue of a heart of the patient in response to rotation of the lead about the longitudinal axis while at least a portion of the lead is positioned substantially parallel to an epicardium of the patient.

3. The device of claim 2, wherein the cardiac tissue comprises the epicardium.

4. The device of claim 1, wherein the width of the first fixation helix increases from the proximal end to the distal end.

5. The device of claim 1, wherein the plurality of electrodes comprises at least one electrode positioned on the housing.

6. The device of claim 1, wherein the first fixation helix comprises one of the plurality of electrodes.

7. The device of claim 1, wherein the first fixation helix and the second fixation helix are configured to engage cardiac tissue of a heart of the patient in response to rotation of the lead about the longitudinal axis while at least a portion of the lead is positioned substantially parallel to the epicardium.

8. The device of claim 1, wherein the cardiac tissue comprises the epicardium.

9. The device of claim 1,
    wherein the distal end of the pulse generator comprises at least one first connector tab,
    wherein the lead further comprises a connector segment defining a proximal end and a distal end,
    wherein the distal end of the connector segment is configured to receive the proximal end of the elongate body and the proximal end of the connector segment comprises at least one second connector tab, and
    wherein the first and second connector tabs are configured to be engaged by rotation of the connector segment about the longitudinal axis of the lead relative to the housing to attach the connector segment to the pulse generator.

\* \* \* \* \*